United States Patent
McCord

(10) Patent No.: US 11,638,759 B2
(45) Date of Patent: May 2, 2023

(54) NON-ACTIVATED, AMORPHOUS, PH NEUTRAL, TWO-PART BEDSIDE-READY CLAY DELIVERY SYSTEM THAT TREATS PATHOGEN INFECTIONS IN HUMANS AND ANIMALS

(71) Applicant: Darlene E. McCord, Coralville, IA (US)

(72) Inventor: Darlene E. McCord, Coralville, IA (US)

(73) Assignee: Darlene E. McCord, Chattanooga, TN (US)

( * ) Notice: Subject to any disclaimer, the term of this patent is extended or adjusted under 35 U.S.C. 154(b) by 112 days.

(21) Appl. No.: 16/947,698

(22) Filed: Aug. 13, 2020

(65) Prior Publication Data

US 2021/0046186 A1     Feb. 18, 2021

Related U.S. Application Data

(60) Provisional application No. 62/885,986, filed on Aug. 13, 2019.

(51) Int. Cl.
*A61K 8/11*     (2006.01)
*A61K 8/31*     (2006.01)
(Continued)

(52) U.S. Cl.
CPC ............ *A61K 47/46* (2013.01); *A61K 9/0014* (2013.01); *A61K 9/06* (2013.01); *A61K 31/05* (2013.01);
(Continued)

(58) Field of Classification Search
None
See application file for complete search history.

(56) References Cited

U.S. PATENT DOCUMENTS

| | | |
|---|---|---|
| 2004/0157766 A1 | 8/2004 | Embil et al. |
| 2010/0130910 A1 | 5/2010 | Berenson |
| 2012/0219497 A1 | 8/2012 | Wellisz et al. |
| 2013/0004544 A1 | 1/2013 | Metge et al. |
| 2016/0263007 A1* | 9/2016 | Strand ...................... A61K 8/24 |

FOREIGN PATENT DOCUMENTS

| | | |
|---|---|---|
| KR | 1020160012257 | 2/2016 |
| WO | 2017048925 A1 | 3/2017 |

OTHER PUBLICATIONS

Banai et al., "Influence of Extracellular Magnesium on Capillary Endothelial Cell Proliferation and Migration", Circulation Research, vol. 67, No. 3, pp. 645-650, Sep. 1990.

Carretero, M. Isabel, "Clay minerals and their beneficial effects upon human health: A review", Applied Clay Science, vol. 21, pp. 155-163, 2002.

(Continued)

*Primary Examiner* — Brian Gulledge
(74) *Attorney, Agent, or Firm* — McKee, Voorhees & Sease, PLC

(57) ABSTRACT

Clay delivery systems for providing antimicrobial compositions are provided. The delivery systems include a two-part active excipient system that delivers clay for various applications of use, including topical applications. The two-part delivery system can include a first part comprising suspending agent(s), poloxamer and optionally a gellant, and a second part that is simultaneously delivered therewith comprising one or more nonionic EO-PO block copolymers in a water-based system. The delivery systems beneficially provide clays in a stable system that also unexpectedly accelerate the release of the clay into the water system for activation and delivery that is enhanced by the poloxamers into the tissue or organ of the body in need of treatment thereof.

16 Claims, 3 Drawing Sheets

(51) Int. Cl.
| | |
|---|---|
| A61K 8/33 | (2006.01) |
| A61K 47/46 | (2006.01) |
| A61K 31/05 | (2006.01) |
| A61K 31/7048 | (2006.01) |
| A61P 31/04 | (2006.01) |
| A61K 47/34 | (2017.01) |
| A61K 9/00 | (2006.01) |
| A61K 9/06 | (2006.01) |

(52) U.S. Cl.
CPC .......... *A61K 31/7048* (2013.01); *A61K 47/34* (2013.01); *A61P 31/04* (2018.01)

(56) References Cited

OTHER PUBLICATIONS

Cunningham et al., "pH-Dependent Metal Ion Toxicity Influences the Antibacterial Activity of Two Natural Mineral Mixtures", PLoS ONE, vol. 5, 10 pages, Mar. 1, 2010.
Honnegowda et al., "Role of angiogenesis and angiogenic factors in acute and chronic wound healing", Plast. Aesthet. Res., vol. 2, Issue 5, pp. 243-249, Sep. 15, 2015.
Lansdown et al., "Zinc in wound healing: Theoretical, experimental, and clinical aspects", Wound Repair and Regeneration, vol. 15, pp. 2-16, Oct. 19, 2006.
Lansdown, Alan B., "Calcium: a potential central regulator in wound healing in the skin", Wound Repair and Regeneration, vol. 10, Issue 5, 14 pages, Nov. 4, 2002.
Lin et al., "Zinc in Wound Healing Modulation", Nutrients, vol. 10, Issue 16, 20 pages, Dec. 24, 2017.
Morrison et al., "Mineralogical Variables that Control the Antibacterial Effectiveness of a Natural Clay Deposit", Environ Geochem Health, vol. 36, pp. 613-631, 2014.
Sarsour et al., "MnSOD activity regulates hydroxytyrosol-induced extension of chronological lifespan", AGE, vol. 34, pp. 95-109, 2012.
Serena et al., "Nutrition in patients with chronic non-healing ulcers: a paradigm shift in wound care", Chronic Wound Care Management and Research, vol. 5, pp. 5-9, 2018.
Williams et al., "Killer Clays! Natural antibacterial clay minerals", Mineralogical Society Bulletin, pp. 3-8, Apr. 2004.
Gaskell et al., "Antimicrobial clay-based materials for wound care" Future Medicinal Chemistry, vol. 6, No. 6, pp. 641-655, published online Jun. 4, 2014.
International Searching Authority in connection with PCT/US2020/046109 filed Aug. 13, 2020, The International Search Report and the Written Opinion of the International Searching Authority, or the Declaration, 11 pages, dated Dec. 8, 2020.
Viseras et al., "Clay Minerals in Skin Drug Delivery", Clays and Clay Minerals, vol. 67, pp. 59-71, published online Apr. 5, 2019.
Afriyie-Gyawu, Evans, "Safety and Efficacy of Novasil Clay as a Dietary Supplement to Prevent Aflatoxicosis", A Dissertation submitted to the Office of Graduate Studies of Texas A&M University, 191 pages, Dec. 2004.
Aslam et al., "Combination of Tigecycline and N-Acetylcysteine Reduces Biofilm-Embedded Bacteria on Vascular Catheters", Antimicrobial Agents and Chemotherapy, vol. 51, No. 4, pp. 1556-1558, Apr. 2007.
Aslam et al., "Role of Antibiofilm-Antimicrobial Agents in Control of Device-Related Infections", Int. J. Artif. Organs, vol. 34(9), pp. 752-758, Jan. 5, 2012.
Becker, Lillian C , "Safety Assessment of Glycerin as Used in Cosmetics", Cosmetics Ingredient Review, 32 pages, Nov. 14, 2014.
Bodratti et al., "Formulation of Poloxamers for Drug Delivery", Journal of Functional Biomaterials, vol. 9, 24 pages, Jan. 18, 2018.
Caflisch et al., "Antibacterial activity of reduced iron clay against pathogenic bacteria associated with wound infections", International Journal of Antimicrobial Agents, vol. 52, pp. 692-696, Jul. 18, 2018.
Chen et al., "Hydroxytyrosol prevents dermal papilla cells inflammation under oxidative stress by inducing autophagy", J. Biochem. Mol. Toxicol., 9 pages, Jun. 17, 2019.
Chowdhury et al., "Pluronic Nanotechnology for Overcoming Drug Resistance", Nanomedicine and Nanotoxicology, Chapter 9, pp. 207-237, Aug. 19, 2017.
Cinar, Dursun, "Purification and Antimicrobial Properties of Oleuropein", A Thesis submitted in partial fulfillment for the degree of Doctor of Philosophy at Thames Valley University, 199 pages, Apr. 2009.
Costa et al., "N-acetylcysteine-functionalized coating avoids bacterial adhesion and biofilm formation", Scientific Reports, 13 pages, Nov. 17, 2017.
Damrau, Dr. Fredic, "The Value of Bentonite for Diarrhea", Med. Ann. Dist. Columbia, 11 pages, Jun. 1961.
El-Feky et al., "Effect of Ciprofloxacin and N-acetylcysteine on Bacterial Adherence and Biofilm Formation on Ureteral Stent Surfaces", Polish Journal of Microbiology, vol. 58, No. 3, pp. 261-267, Jul. 27, 2009.
Ghadiri et al., "Biomedical Applications of Cationic Clay Minerals", RSC Advances, 20 pages, Mar. 9, 2015.
Ghalandari et al., "Antimicrobial effect of Hydroxytyrosol, Hydroxytyrosol Acetate and Hydroxytyrosol Oleate on *Staphylococcus aureus* and *Staphylococcus epidermidis*", Electronic Journal of General Medicine, http://www.ejgm.co.uk, 7 pages, Feb. 23, 2018.
"Glycerin", The United States Pharmacopeial Convention, Revisional Bulletin, 2 pages, May 1, 2009.
"Kelco-Vis DG Diutan Gum, Guidelines for Proper Dissolution", CP Kelco, A Huber Company, 2 pages, Jul. 2017.
Louie et al., "Pharmacodynamic Evaluation of the Activities of Six Parenteral Vancomycin Products Available in the United States", Antimicrobial Agents and Chemotherapy, vol. 59, No. 1, pp. 622-632, Jan. 2015.
Moloughney et al., "Poloxamer 188 (P188) as a Membrane Resealing Reagent in Biomedical Applications", Recent Pat Biotechnol., vol. 6(3), pp. 200-211, Dec. 2012.
Moosavi, Maryam, "Bentonite Clay as a Natural Remedy: A Brief Review", Iran J. Public Health, vol. 46, No. 9, pp. 1176-1183, Sep. 2017.
Morrison et al., "Interactions between antibacterial clays and bacteria: Determining the reactivity and geochemistry of transition metals", 2012 Clay Minerals Society Annual Meeting, Powerpoint, 33 pages, 2012.
Morrison, Keith D., "Unearthing the Antibacterial Activity of a Natural Clay Deposit", A Dissertation presented in partial fulfillment of the requirements for the Degree Doctor of Philosophy, Arizona State University, 180 pages, Jun. 2015.
Morrison et al., "Unearthing the Antibacterial Mechanism of Medicinal Clay: A Geochemical Approach to Combating Antibiotic Resistance", Scientific Reports, 13 pages, Jan. 8, 2016.
Morrison et al., "The Anatomy of an Antibacterial Clay Deposit:k A New Economic Geology", Economic Geology, Bulletin of the Society of Economic Geologist, vol. 112, No. 7, pp. 1551-1570, Jun. 30, 2017.
Mousa et al., "Clay nanoparticles for regenerative medicine and biomaterial design: A review of clay bioactivity", Biomaterials, vol. 159, pp. 204-214, 2018.
Mousavi et al., "Development of Clay Nanoparticles Toward Bio and Medical Applications", Current Topics in the Utilization of Clay in Industrial and Medical Applications, Chapter 9, pp. 167-191, Sep. 2018.
Williams et al., "Bentonite, Bandaids, and Borborygmi", Elements (Que), vol. 5(2), pp. 99-104, Apr. 1, 2009.
Omar, Syed Haris, "Oleuropein in Olive and its Pharmacological Effects", Scientia Phamnaceutica, 22 pages, Apr. 23, 2010.
Patel et al., "Poloxamers: A pharmaceutical excipients with therapeutic behaviors", International Journal of PharmTech Research, vol. 1, No. 2, pp. 299-303, Apr. 2009.
"Preclinical Safety Results", Phrixus Pharmaceuticals Inc., 2 pages, accessed on the internet on Jul. 26, 2019.
Pray, Leslie, "Antibiotic Resistance, Mutation Rates and MRSA", Nature Education, vol. 1(1):30, 4 pages Jul. 30, 2019.

(56) References Cited

OTHER PUBLICATIONS

Sircar et al., "High Performance Liquid Chromatography Analysis and Anti-Methicillin Resistant *Staphylococcus aureus* Activity of Olive Fruit Ethanolic Extract", International Research Journal of Pharmacy, vol. 8(7), pp. 126-130, Jul. 29, 2017.
McIntyre, Tyler, "Explanation of Shear, Temperature, and Viscosity in Petrolatum Containing Systems", Email from Petrolia Technical Team of Sonnebom LLC to Dr. McCord, 4 pages, Jun. 30, 2017.
Sudjana et al., "Antimicrobial activity of commercial *Olea europaea* (olive) leaf extract", International Journal of Antimicrobial Agents, vol. 33, pp. 461-463, 2009.
Williams et al., "Evaluation of the medicinal use of clay minerals as antibacterial agents", Int. Geol. Rev., vol. 52 (7/8), pp. 745-770, Jul. 1, 2010.
Williams, Lynda B., "Geomimicry: harnessing the antibacterial action of clays", Clay Minerals, vol. 52, 24 pages, Jan. 16, 2017.
Williams et al., "What Makes a Natural Clay Antibacterial?", Environ. Sci. Technol., vol. 45(8), pp. 3768-3773, Apr. 15, 2011.
Xu et al., "Rheological properties and thickening mechanism of aqueous diutan gum solution: Effects of temperature and salts", Carbohydrate Polymers, vol. 132, pp. 620-629, Jun. 23, 2015.
Rondeau, Virginie, "A review of epidemiologic studies on aluminum and silica in relation to Alzheimer's disease and associated disorders", Rev. Environ. Health, vol. 17(2), pp. 107-121, 2002.
Schumann, Klaus, "Safety Aspects of Iron in Food", Annals of Nutrition and Metabolism, vol. 45, pp. 91-101, May 2001.
"ToxGuide for Aluminum Al", US Dept. of Health and Human Services, pamphlet, 2 pages, Sep. 2011.
Basf, "Novasil(tm) Plus", Pocket Guide, 2 pages, Dec. 2015.

\* cited by examiner

US 11,638,759 B2

NON-ACTIVATED, AMORPHOUS, PH NEUTRAL, TWO-PART BEDSIDE-READY CLAY DELIVERY SYSTEM THAT TREATS PATHOGEN INFECTIONS IN HUMANS AND ANIMALS

CROSS-REFERENCE TO RELATED APPLICATION

This application claims priority under 35 U.S.C. § 119 to Provisional Application U.S. Ser. No. 62/885,986, filed on Aug. 13, 2019, which is herein incorporated by reference in its entirety including without limitation, the specification, claims, and abstract, as well as any figures, tables, or examples thereof.

FIELD OF THE INVENTION

The invention relates to clay delivery systems for providing antimicrobial compositions. The delivery systems include a two-part active excipient system that delivers clay for applications of use, including for example topical applications. The two-part delivery system can include a first part comprising suspending agent(s), poloxamer and a gellant, and a second part that is simultaneously delivered therewith comprising one or more nonionic block EO-PO copolymers in a water-based system. The delivery systems beneficially provide clays in a stable system that also unexpectedly accelerate the release of the clay into the water system for activation and delivery that is enhanced by the poloxamers onto a tissue of the body, including skin and wounds, mucosal cells, intestinal track, ear canal, nasal passages and oral cavities in need of treatment thereof.

BACKGROUND OF THE INVENTION

The beneficial health effects of clays, including its antimicrobial properties have been widely researched for current and potential biomedical applications. Research done at Arizona State University's School of Earth and Space Exploration (SESE) by Lynda Williams, et al, determined that blue clay's mechanism of action is like the "Trojan Horse" attack in ancient Greece, whereby two elements in the clay work in tandem to kill bacteria. One of the metallic elements in blue clay is chemically reduced iron, which in small amounts is required by a bacterial cell for nutrition. The "Trojan Horse" tricks the cell into opening its outer wall. Then aluminum, another element found in blue clay, props the cell wall open, allowing a flood of iron to enter the cell. This overabundance of iron then poisons the cell, killing it as the reduced iron becomes oxidized. Although studies have been conducted exploring the potential antibacterial properties of natural clays, these studies have not determined how to use clays as delivery systems or in delivery systems for applications of use for antimicrobial treatments and for the ability to store stable compositions containing clays. Instead, the conventional use of clays includes the mixing of clay with water to form a paste or gel that is simply applied externally. This activation of clay's antimicrobial activity when in contact with water then rapidly results in the activity of clay being exhausted within about 24 hours, significantly limiting its use in various settings.

Clays may be classified or referred to as natural minerals having particulate diameters of <2 μm. Although natural clays have been studied for pathogenic activity, only certain clays are antibacterial, and even less are bactericidal. Clays that have been identified as potentially having antibacterial properties share mineralogical and chemical compositions that impact the buffering capacity of fluids in contact with the clay, include reduced transition metals (most commonly $Fe^{2+}$), and have the capability of impacting water chemistry due to its large surface area.

Clays having pathogenic activity include those containing soluble reduced metals and expandable clay minerals that absorb cations. Such properties allow for extended metal release and the production of toxic hydroxyl radicals. Examples of soluble reduced metals include soluble $Fe^{2+}$ and $Al^{3+}$ which target multiple cellular systems in pathogens, leading to bactericidal activity. These soluble reduced metals contribute to the bactericidal mechanism through misfolding cell membrane proteins, and evoking membrane oxidation and causing a hydroxyl radical attack on pathogenic intracellular proteins and DNA.

Among clays that have been studied for antibacterial activity, blue clay has attracted interest for its ability to kill pathogens through chemical toxicity, rather than through the physical disruption of cells. Blue clay (a clay from Oregon naturally containing about 10% pyrite) has been determined to be bactericidal. When clays containing reduced transition metals are contacted with oxygenated water, soluble metals from the minerals likely provide aqueous reactants that drive an antibacterial process. A proposed general mechanism of action for the antibacterial properties of blue clay is that when the clay is hydrated, this results in the release of elements such as iron (particularly reduced $Fe^{2+}$) and aluminum (particularly $Al^{3+}$), causing toxicity to bacteria through damaging bacterial membranes. The damage in membranes then allows for the excess iron to cause intracellular protein damage through oxidation.

Blue clay has further been studied for its beneficial antibacterial effects against a broad spectrum of bacteria, including antibiotic-resistant strains. Blue clay has been studied for its antimicrobial efficacy against bacteria such as staphylococci, streptococci, Enterobacteriaceae and non-fermenting Gram-negative bacilli, to name a few. Blue clay has further been studied for its superior antibacterial activity against bacteria such as E. coli and methicillin-resistant Staphylococcus aureus (MRSA). The conventional treatment option for MRSA infections is currently vancomycin, however, there is a growing number of physicians prescribing newer antibiotic alternatives, such as quinupristin-dalfopristin, linezolid, and daptomycin. However, MRSA continues to challenge the medical industry in continuing to cause deaths not only within hospitals, but also with a growing number of MRSA infections occurring outside the hospital as well.

MRSA is not the only challenge to the medical industry. The World Health Organization (WHO) is warning if nothing is done the world is heading for a 'post-antibiotic' era as the most common of infections, such as chlamydia, will lack effective treatment options. The WHO estimates that "superbugs" could kill 10 million a year by 2050 from infections that are treatable today. Accordingly, there is a need for providing distinct treatment options for such threats. There is an insufficient development of effective drug options to keep up with the threat of how fast bacteria are evolving to resist them.

While research has demonstrated significant reduction of bacterial population size with the application of antimicrobial clays, such as blue clay, there remains a need for developing drug delivery systems, including those that are bedside ready, allowing for the activation of the antimicrobial constituents of clay, and which are both shelf stable and medically acceptable (including sterile and effective). Further, there remains a need for providing alternative treatments for treating MRSA infections, a highly drug-resistant bacteria that is known to double every half hour when living in optimal conditions (e.g. a wound).

Further, current pharmaceuticals available to treat various types of infections include various types of therapeutic agents, such as antibiotics. The route of administration for such antibiotic treatments can vary, where some are prescribed to be taken orally, some to be applied topically, while others to be administered intravenously. However, as the use of conventional antibiotics increases for controlling bacteria, the increasing emergence of antibiotic-resistant strains of pathogenic bacteria is becoming an increasing issue. Additionally, antibiotic resistance is reducing the effectiveness of some antibiotics used to fight bacterial infections. The evolution of resistant strains of bacteria is a natural phenomenon that occurs when bacteria are exposed to antibiotics, and resistant traits can be exchanged between certain types of bacteria, leading to drug resistance. Therefore, compositions, systems, and methods of delivering effective treatment doses of antimicrobials, while addressing antibiotic resistance are still needed.

It is therefore an object of this disclosure to provide stable clay delivery systems that are bedside ready utilizing antimicrobial clays for antimicrobial compositions and applications of use. As referred to herein, bedside ready refers to packaging, storage and ongoing use of a delivery system by a care provide and/or patient without the need to formulate the composition, as it is provided in a stable system ready for use.

It is a further object of the disclosure to provide pharmaceutical compositions utilizing a clay delivery system for delivering therapeutic agents through various applications, including topical applications of use.

It is a still further object of the disclosure to provide pharmaceutical compositions utilizing a clay delivery system providing safe an effective dosing of clay to ensure constituent ingredients in drugs (21 CFR 610.15) are provided for various applications of use.

It is a further object of the disclosure to provide pharmaceutical compositions utilizing a clay delivery system for reducing antibiotic resistance by effectively eliminating difficult to treat bacteria.

It is another object of this disclosure to formulate antimicrobial compositions utilizing a clay delivery system with antibiotics to reduce antibiotic drug resistance.

Other objects, aspects and advantages of this invention will be apparent to one skilled in the art in view of the following disclosure, the drawings, and the appended claims.

SUMMARY OF THE INVENTION

An aspect of the invention encompasses a delivery system for clay comprising a housing containing a two-part active excipient system comprising a first part and a second part; wherein the first part comprises clay, glycerin (or other suspending agent), a nonionic block EO-PO copolymer, and optionally a gellant; and wherein the second part comprises at least one nonionic block EO-PO copolymer in a pH neutral water-based system, and wherein the ratio of the first part to the second part is from about 1:1 to about 9:1.

In further embodiments, clay compositions comprise: a two-part active excipient clay delivery system comprising a first part and a second part; and optionally a therapeutic agent; wherein the first part comprises sterilized clay, suspending agent(s), a nonionic block EO-PO copolymer, and optionally a gellant; and wherein the second part comprises at least one nonionic block EO-PO copolymer in a pH neutral water-based system, and wherein the ratio of the first part to the second part is from about 1:1 to about 9:1.

In further embodiments, a method for delivering a clay composition for topical applications of use comprises: combining parts of a two-part active excipient clay composition, wherein the first part comprises sterilized clay, suspending agent(s), a nonionic block EO-PO copolymer, and optionally a gellant, and wherein the second part comprises at least one nonionic block EO-PO copolymer in a pH neutral water-based system, and wherein the ratio of the first part to the second part in the composition is from about 1:1 to about 9:1; accelerating the release of the clay into the water-based system; activating the clay; and delivering the clay composition to a surface.

In still further embodiments, a method for using a clay delivery system for antimicrobial treatment comprises: combining parts of a two-part active excipient clay composition, wherein the first part comprises sterilized clay, suspending agent(s), a nonionic block EO-PO copolymer, and optionally a gellant, and wherein the second part comprises at least one nonionic block EO-PO copolymer in a pH neutral water-based system, and wherein the ratio of the first part to the second part in the composition is from about 1:1 to about 9:1; accelerating the release of the clay into the water-based system; activating the clay; and delivering the clay composition to a tissue or organ of the body.

Yet another aspect of the invention encompasses a pharmaceutical composition for providing antimicrobial treatment with the clay delivery system. Another aspect of the invention encompasses methods of delivering a clay composition for topical applications of use. A further aspect of the invention encompasses methods of treating infections with antimicrobial treatment compositions utilizing a clay delivery system.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

Figure 1A:
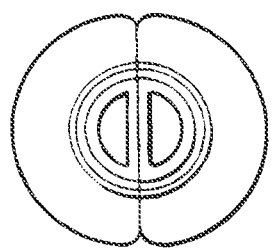
FIGS. 1-3 show exemplary dual-chamber dispensers suitable for use in storage and dispensing of the clay delivery systems and pharmaceutical compositions described herein, including a dual chamber tube shown in two views (FIGS. 1A, 1B), dual chamber sachet (FIG. 2), and a dual chamber syringe shown in two views (FIGS. 3A, 3B).

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENTS

The embodiments are not limited to particular delivery systems, compositions, methods of treatment, and methods of use thereof, which can vary and are understood by skilled artisans. It has been surprisingly found that the delivery systems beneficially provide clays in a stable system, such as a system that controls the contacting of a first part of the system containing clay with a second part of the system containing water, and such controlled or designed release of the clay into water provides a mechanism to control the timed release and significantly expands the opportunity going use of the clay systems, including settings such as hospitals and extended care. It has also been surprisingly found that the delivery systems unexpectedly accelerate the release of the clay into the water system for activation and delivery that is enhanced by the poloxamers onto a tissue of the body, including skin, mucosal membranes and organs in need of treatment thereof.

It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments without undue experimentation, but the preferred materials and methods are described herein. In describing and claiming the embodiments, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

The term "antimicrobial" is defined herein to mean a composition that inhibits the growth of, or kills, organisms including bacteria, protozoans, viruses, yeast, fungi, or other infectious agents.

In the present invention, an "effective amount" or "therapeutically effective amount" of a compound or of a composition of the present invention is that amount of such compound and/or composition that is sufficient to effect beneficial or desired results as described herein. In terms of treatment of a mammal, e.g., a human patient, an "effective amount" is an amount sufficient to treat, reduce, manage, palliate, ameliorate, or stabilize a condition, such as a non-congenital oncosis or extended quiescence of the cells of a mammal, or both, as compared to the absence of the compound or composition.

The terms "include" and "including" when used in reference to a list of materials refer to but are not limited to the materials so listed.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions may comprise, consist essentially of, or consist of the components and ingredients as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Clay Delivery Systems

According to embodiments, the clay delivery systems are a two-part delivery system. The bedside ready clay delivery system has two parts; a first part comprising clay, suspending agent(s) such as PEG or glycerin, a nonionic block EO-PO copolymer, and an optional gellant, and a second part comprising at least one nonionic block EO-PO copolymer in a pH neutral water-based system. As referred to herein, pH neutral (also referred to as pH balanced) is from about 6-8, preferably about 7. The second part may optionally comprise a preservative system.

Exemplary clay delivery systems are shown in Tables 1A-1B in weight percentage. In an aspect, the first part delivery system comprises from about 20 wt-% to about 80 wt-% or preferably about 50 wt-% of the clay delivery system, and the second part delivery system comprises from about 20 wt-% to about 80 wt-% or preferably about 50 wt-% of the clay delivery system. Without being limited according to the invention, all ranges within the weight percentages are further included within the scope of the invention. In a preferred embodiment, the clay delivery systems are dosed in about equal parts (50 wt-%-50 wt %) and have similar viscosities to facilitate such dispensing (i.e. evacuating or dispensing from a housing simultaneously).

The clay delivery systems have viscosities that allow dispensing with little mechanical force. They are not semi-solids, such as those common in the use of thickened pastes, poultices or liniments. The ratio of the first part delivery system to the second part delivery system will depend upon the form of the delivery system, such as differences between topical and oral delivery. In some embodiments a ratio of the first part to the second part is about 1:1, 2:1, 3:1, 4:1, 5:1, 6:1, 7:1, 8:1, or 9:1, or any range therebetween.

TABLE 1A

| Material | First Exemplary Range wt.-% | Second Exemplary Range wt.-% | Third Exemplary Range wt.-% |
|---|---|---|---|
| First Part Delivery System | 20-90 | 40-60 | 50 |

TABLE 1A-continued

| Material | First Exemplary Range wt.-% | Second Exemplary Range wt.-% | Third Exemplary Range wt.-% |
|---|---|---|---|
| Second Part Delivery System | 10-80 | 40-60 | 50 |

According to embodiments, the two-part clay delivery systems include a first part comprising clay, suspending agent(s), a nonionic block EO-PO copolymer, and an optional gellant, and a second part comprising at least one nonionic block EO-PO copolymer in a water-based system. The second part can further comprise additional additives (e.g. solvents, viscosity adjustment agents, preservatives). Exemplary clay delivery systems are shown in Table 1B in weight percentage.

Beneficially, the clay component is not formulated with water containing components in the first part of the delivery system. The significant use of prior compositions containing clays and aqueous or water-containing components, including hydrogels, undesirably results in a non-stable composition, such as less than 24 hour stability. Unlike these compositions the clay delivery system provides long-term stability as a result of not contacting the clay with water in the first part of the delivery system.

Figure 1B:
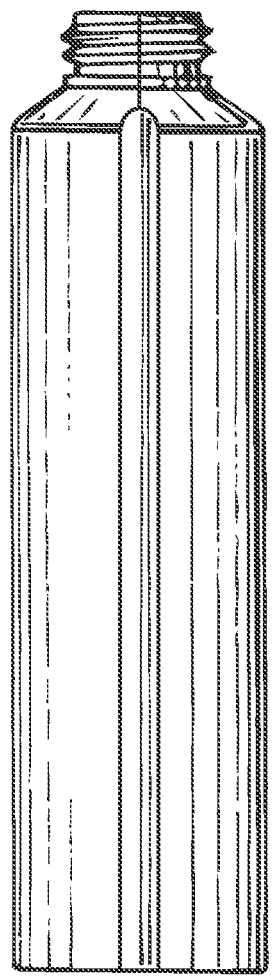
Figure 2:
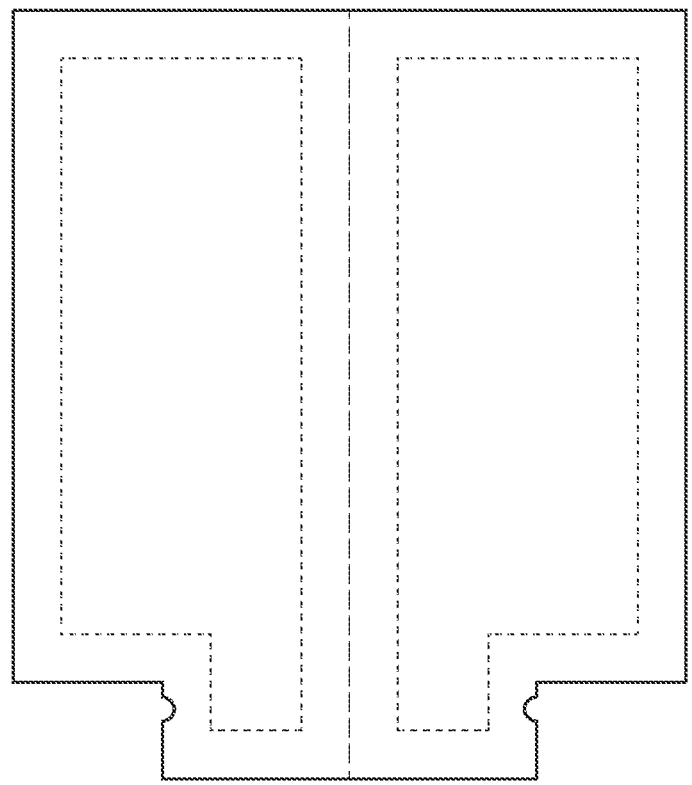
Figure 3A:
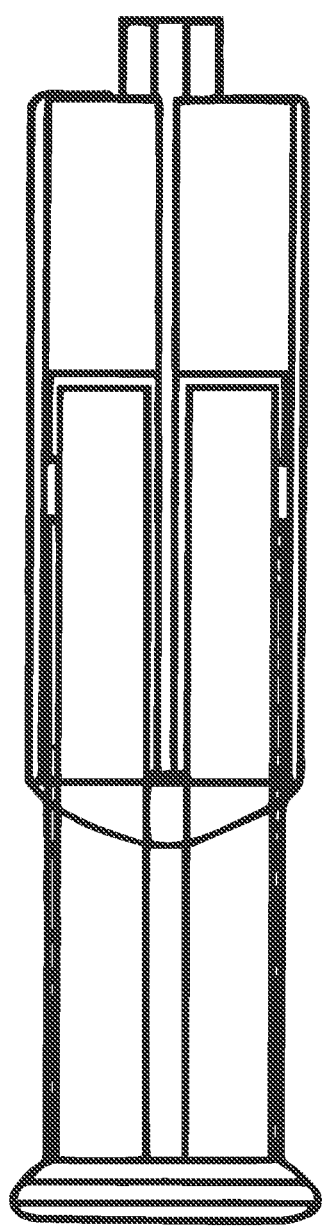
Figure 3B:
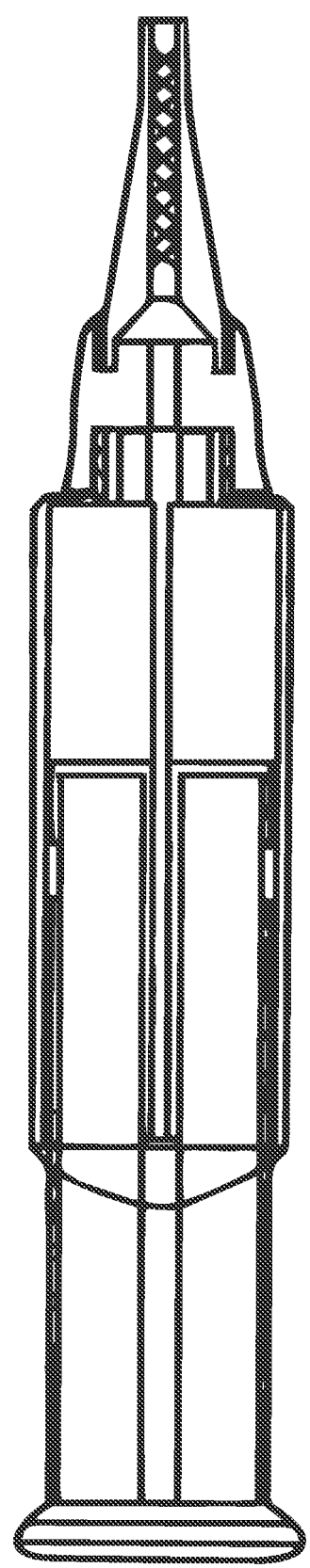

In an embodiment, the two-part delivery system is provided in a dual chamber dispensing device, such as a dual chamber tube (FIGS. 1A-1B), dual chamber sachet (FIG. 2), or a dual chamber syringe (FIGS. 3A, 3B). Each exemplary dispensing device is well suited for storage of the delivery system that provides separation of the first and second parts of the clay delivery system. However, in the various depicted examples, the two parts can be combined for simultaneous dispensing in equal parts. For example, the sachet can be a foil sachet that when folder in half the two parts can be squeezed to push out the two parts simultaneously. According to embodiments, the clay is present in the first part of the two-part delivery system to prevent premature activation from hydration from the water-based system in the second part of the two-part delivery system. The nonionic block E0-PO copolymer in the first part then accelerates the release of clay into the water system of the second part for activation of the clay and enhanced delivery by the at least one nonionic block EO-PO copolymer(s) in the second part.

Beneficially, the two-part delivery systems allow for controlled application and providing desired dosing of actives contained therein. For example, certain components in the clay are to be dosed at appropriate levels based primarily on the subject's body weight (e.g. aluminum, iron, pyrite).

As a further benefit the two-part delivery system allows for the delivery of composition wherein different components have distinct viscosity and/or other characteristics. For example, in an embodiment, a first part delivery system containing the clay has an increased viscosity in comparison to the second part delivery system containing at least one nonionic block EO-PO copolymer in a water-based system. In an embodiment, the first part delivery system can have a viscosity in the range of about 20,000 centipoise (cP) to about 50,000 cP, or from about 25,000 cP to about 40,000 cP, or from about from about 30,000 cP to about 40,000 cP, or at least about 20,000 cP, at least about 25,000 cP, at least about 30,000 cP, or at least about 35,000 cP. In an embodiment, the second part delivery system can have a viscosity in the range of about 5,000 cP to less than about 20,000 cP, or from about 10,000 cP to less than about 20,000 cP, or from about from about 15,000 cP to less than about 20,000 cP, or less than about 20,000 cP, less than about 19,000 cP, less than about 18,000 cP, less than about 17,000 cP, less than about 16,000 cP, or less than about 15,000 cP.

TABLE 1B

| Material | First Exemplary Range wt.-% | Second Exemplary Range wt.-% | Third Exemplary Range wt.-% |
|---|---|---|---|
| First Part Delivery System | | | |
| Suspending agent(s) | 20-80 | 30-80 | 35-80 |
| Nonionic block EO-PO copolymer(s) (in First Part Delivery System) | 3-25 | 5-20 | 10-20 |
| Gellant | 0-20 | 0.01-10 | 0.1-1 |
| Clay | 10-50 | 15-40 | 20-35 |
| Second Part Delivery System | | | |
| Nonionic block EO-PO copolymer(s) (in Second Part Delivery System) | 3-35 | 10-30 | 10-27 |
| Additional Additives (e.g. solvents, viscosity adjustment agents, preservatives) | 0-5 | 0-2 | 0.01-2 |
| Water | 50-90 | 60-90 | 70-90 |

In an embodiment, the delivery systems and pharmaceutical compositions incorporating the delivery systems can be provided in various delivery forms. In an embodiment, the delivery system and/or pharmaceutical compositions are provided as ointments, creams, lotions, solution, suspension, emulsion, pastes, gels or gel sheets, syrups, or the like. In preferred embodiments, the delivery system and/or pharmaceutical compositions are provided as ointments, creams, pastes, lotions, solution, suspension, emulsion, gels or gel sheets, or syrups.

Suspending Agents

The clay delivery systems include glycerin (or another suspending agent such as polyethylene glycol). Glycerin is a hydrocarbon structure having hydroxy functional groups, namely a polyhydric alcohol as shown in the following formula:

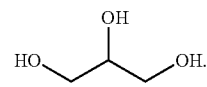

Glycerin has functionality as an emollient and having therapeutic effectiveness against dry skin by limiting the amount of water loss from skin. The glycerin functions as a thick, adhesive and barrier layer over the skin to aid in binding moisture to the skin or treated surface (such as a tissue or organ of the body). In one aspect of the invention, glycerin is used for suspending the components of the first part delivery system and maintaining a stable suspension. The glycerin further provides hydration to the clay to remain hydrate for activation when combined with the water of the second part of the delivery system. Glycerin further may function as an anti-irritant in reducing skin irritation for topical formulations. Each of these mechanisms of the glycerin is important for the storage, stability and delivery of the clay actives, in particular in embodiments of use where the clay delivery system is applied to damaged tissues or organs where hydration is beneficial as opposed to drying out of the tissue or organ.

In embodiments where the clay delivery systems include a non-glycerin suspending agent, exemplary suspending agents include for example, propylene glycol, polyethylene glycol (PEG, poly(ethylene oxide), polyoxyethylene, H—(O—CH$_2$—CH$_2$)$_n$—OH) or propanediol. In an embodiment, polyethylene glycol has an average number of ethylene glycol units of at least about 2, 3, 4, 5, 6, 7, 8, 9, 10, or more. In a preferred embodiment, PEG-8 is a suitable polyethylene glycol.

In some embodiments, the suspending agent(s) is included in the clay delivery system in an amount of at least about 20 wt-% to about 80 wt-%, about 30 wt-% to about 80 wt-%, or about 35 wt-% to about 80 wt-%. In addition, without being limited according to the invention, all ranges recited are inclusive of the numbers defining the range and include each integer within the defined range.

Nonionic Block EO-PO Copolymers

The clay delivery systems include nonionic block EO-PO copolymers (also includes poly (ethylene oxide) (PEO)-poly (propylene oxide) (PPO) copolymers) in both the first part delivery system and second part delivery system. In embodiments, the nonionic block EO-PO copolymers include, but are not limited to, poloxamers. These poloxamers are odorless, tasteless, white, waxy granules with free-flowing properties. Poloxamers are amphiphilic in nature, as they are soluble in both polar and nonpolar solvents. The amphiphilic properties stem from a tri-block configuration, consisting of a hydrophobic unit [poly (propylene oxide) (PPO)] in between two hydrophilic units [poly (ethylene oxide) (PEO)] with the basic sequence of A-B-A and having the structure (PEO$_a$-PPO$_b$-PEO$_a$) shown below:

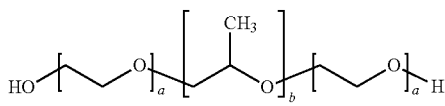

Exemplary poloxamers and the number and average size of EO/PEO and PO/PPO blocks include those shown by Chowdhury P. et al., *Pluronic Nanotechnology for Overcoming Drug Resistance*. In: Yan B. et al. (eds) Bioactivity of Engineered Nanoparticles (2017), which is reproduced below as Table 2:

TABLE 2

| Name | Average Molecular Weight (g/mol) | No. of EO units | No. of PO units |
|---|---|---|---|
| Poloxamer 124 (Pluronic ® L-44) | 2090-2360 | 12 | 20 |
| Poloxamer 188 (Pluronic ® F-68) | 7680-9510 | 80 | 27 |
| Poloxamer 237 (Pluronic ® F-87) | 6840-8830 | 64 | 37 |
| Poloxamer 338 (Pluronic ® F-108) | 12700-17400 | 141 | 44 |
| Poloxamer 407 (Pluronic ® F-127) | 9840-14600 | 101 | 56 |
| Poloxamer 401 (Pluronic ® L121) | 4400 | 10 | 68 |
| Poloxamer 184 (Pluronic ® L-64) | 2900 | 26 | 30 |

Additional exemplary poloxamers include Poloxamer 105 having a molecular structure: polymer with oxirane (11; 16) where oxirane means ethylene oxide, also described as EO$_{27}$PO$_{56}$EO$_{27}$. Further Poloxamer 85 has a molecular structure: triblock copolymer with central chain of poly (propylene oxide) (70 units) flanked by two hydrophilic chains of poly(ethylene oxide) (20 units), function: surfactant.

These EO-PO copolymers have the same chemical structure but differ in the number of EO/PEO and PO/PPO units, as well as in molecular weight. Due to the hydrophobic and hydrophilic nature of the poloxamers, the amphiphilic properties of poloxamers differ depending on the number of EO/PEO or PO/PPO units, and can be determined by the hydrophilic-lipophilic balance (HLB) of the poloxamer.

In embodiments, the nonionic block EO-PO copolymer in the first part has the formula PEO$_a$PPO$_b$-PEO$_a$, where the sum of a=70-120 and b=40-65. In other embodiments, the at least one nonionic block EO-PO copolymer in the second part has the formula PEO$_a$-PPO$_b$-PEO$_a$, where the sum of a=70-120 and b=40-65 and/or has the formula PEO$_a$-PPO$_b$-PEO$_a$, where the sum of a=70-100 and b=20-35.

In other embodiments, suitable surfactants include a diblock polymer comprising a PEO block and a PPO block, a center block of polyoxypropylene units (PPO), and having blocks of polyoxyethylene grafted onto the polyoxypropylene unit or a center block of PEO with attached PPO blocks. Further, this surfactant can have further blocks of either polyoxyethylene or polyoxypropylene in the molecules. A suitable average molecular weight range of useful surfactants can be about 1,000 to about 40,000 and the weight percent content of ethylene oxide can be about 20-90 wt-%. In embodiments, the first part delivery system comprises a nonionic EO-PO copolymer having an average molecular weight of from about 5,000 to about 20,000 and a weight percent content of ethylene oxide of from about 50-80 wt-%. In embodiments, the second part delivery system comprises at least one nonionic EO-PO copolymer having an average molecular weight of from about 5,000 to about 20,000 and a weight percent content of ethylene oxide of from about 60-90 wt-%, and in preferred embodiments, the second part delivery system comprises at least two nonionic EO-PO copolymers, each having an average molecular weight of from about 5,000 to about 20,000 and a weight percent content of ethylene oxide of from about 60-90 wt-%.

In further embodiments, the nonionic block EO-PO copolymer in the first part is poloxamer 407 and/or poloxamer 188. In even further embodiments, at least one nonionic block EO-PO copolymer in the second part is poloxamer 407 and/or poloxamer 188. In still further preferred embodiments, the nonionic block EO-PO copolymer in the first part is poloxamer 407 and poloxamer 188, and the second part contains the nonionic block EO-PO copolymer comprising poloxamer 188. Without being limited to a particular mechanism of action, the use of the nonionic block EO-PO copolymers beneficially control and enhance release of the clay when the first part of the system contacts the second part of the system containing water. Further, the nonionic block EO-PO copolymers, in particular the poloxamer 407 is particularly effective at taking therapeutic agents into bacteria and killing the bacteria to provide toxicity to the cells. In preferred embodiments, such as the combined use of the poloxamer 407 with poloxamer 188, which has efficacy in the second part of the system for repairing cell membranes and reducing inflammation, the two-part system facilitates efficacious antimicrobial efficacy while reducing inflammation.

In some embodiments, the first part delivery system comprises at least one nonionic block EO-PO copolymer, and the second part delivery system comprises at least one nonionic block EO-PO copolymer. In preferred embodiments, the first part delivery system comprises at least two nonionic block EO-PO copolymers, and the second part delivery system comprises at least one nonionic block EO-PO copolymers. In further preferred embodiments, the first part delivery system comprises at least one nonionic block EO-PO copolymer, and the second part delivery system comprises at least two nonionic block EO-PO copolymers. The nonionic block EO-PO copolymers in the first part and second part may be of the same type of nonionic block EO-PO copolymer, or may be different types of nonionic block EO-PO copolymers.

In some embodiments, the nonionic block EO-PO copolymer is included in the first part of the two-part clay delivery system in an amount of at least about 3 wt-% to about 25 wt-%, about 5 wt-% to about 20 wt-%, or about 10 wt-% to about 20 wt-%. In addition, without being limited according to the invention, all ranges recited are inclusive of the numbers defining the range and include each integer within the defined range.

In some embodiments, at least one nonionic block EO-PO copolymer is included in the second part of the two-part clay delivery system in an amount of at least about 3 wt-% to about 35 wt-%, about 10 wt-% to about 30 wt-%, or about 10 wt-% to about 27 wt-%. In addition, without being limited according to the invention, all ranges recited are inclusive of the numbers defining the range and include each integer within the defined range.

Without being limited to a particular mechanism of action of the clay delivery system, further formulation designs to include certain poloxamers are required. For example, it is not desirable to include poloxamers in any petrolatum as this presents significant safety concerns due to formation of glass like shards. Accordingly the precise combination of the first and second parts of the delivery system are required for both the stability of the clay and the safety of the delivery system itself.

Gellant

The clay delivery systems and antimicrobial compositions disclosed herein can include a gellant in addition to the nonionic block EO-PO copolymers (some of which are also functioning as gellants). In embodiments, the clay delivery systems and compositions comprise a safe and effective amount of a pharmaceutically acceptable carrier, suitable for topical application to the tissue of the body or targeted organs within which the essential and optional materials are delivered at an appropriate concentration. The gellant can thus act as a carrier, dispersant, suspending agent, stabilizing agent structuring agent, or the like for the active ingredients of the composition. The gellant ensures that the active ingredients of the composition can be suspending in the clay and thereafter applied to and distributed evenly over the selected target surface at an appropriate concentration as a result of the gallant maintaining the clay distributed within the suspending agent.

The gellant is physically and chemically compatible with the essential components described herein, and should not unduly impair stability, efficacy or other use benefits associated with the compositions of the present invention. Suitable gellants of the present invention include polysaccharides and gums. Exemplary polysaccharides include linear sulfated polysaccharides. Exemplary gums include pectin, lignin, algin, gums and agar-agar. In a preferred embodiment, carrageenan is employed as the gellant.

Without being limited to a particular mechanism of action, the use of the gallant, such as carrageenan, does not require water to provide a suspension of the clay in the glycerin (or other suspending agent). Beneficially this does not allow the clay to react and provides stable storage conditions to enable the providing of a bedside ready delivery system.

In some embodiments, certain nonionic block EO-PO copolymers can function as gellants (e.g. Poloxamer 407) and no additional gellant is required. In other embodiments where alternative nonionic block EO-PO copolymers are selected, a gellant is desired in the clay delivery system.

In some embodiments, the gellant is included in the clay delivery system in an amount of at least about 0 wt-% to about 20 wt-%, about 0.01 wt-% to about 10 wt-%, or about 0.1 wt-% to about 10 wt-%. In addition, without being limited according to the invention, all ranges recited are inclusive of the numbers defining the range and include each integer within the defined range.

Clay

The clay delivery systems include a source of clay. In embodiments, the clay is present in the first part of the two-part delivery system. The presence of the clay within the first part of the system prevents the clay from premature activation from hydration. The nonionic block EO-PO copolymers of the suspending agent(s) base accelerates the release of the clay from the first part into the water system of the second part, where the clay is activated. Suitable clays include, but are not limited to, a natural clay or clay mineral and/or synthetic clay or clay mineral, or other suitable materials having clay-like properties.

Clays include a variety of natural mineral made up of crystalline material. Clay minerals have a sheet-like structure and are composed of mainly silicate and aluminate groups. In some embodiments, the clays are predominantly layered silicate structures. Exemplary groups include bentonites, smectite, illite-smectite, pyrite, silicates, e.g. aluminum silicates, magnesium aluminum silicates, magnesium trisilicates, and the like. The clays can be hydrated. In some embodiments the clays are polycationic compounds. In preferred embodiments, the clays are amorphous and do not have a rigid structure.

In exemplary embodiments, the clay is a naturally mined antimicrobial clay known as Blue clay. The source of the Blue clay is an open pit mine in hydrothermally altered, pyroclastic material in the Cascade Mountains. The clay is dominated by illite-smectite (a group of clay minerals having an expandable interlayer structure) pyrite, Ca-plagioclase, and quartz. The expandable smectite interlayer region functions like a reservoir from which metals, which may have antibacterial effects, are slowly released via cation exchange. The antibacterial activity of the Blue clay has been shown to completely eliminate *Escherichia coli, Staphylococcus aureus, Pseudomonas aeruginosa, Salmonella typhimurium*, and antibiotic resistant extended-spectrum beta lactamase (ESBL) *E. coli* and methicillin resistant *S. aureus* (MRSA) within 24 hours invitro. Without wishing to be bound by theory, the antibacterial properties of the Blue clay may be due to a rare antimicrobial transition metal combination, including a level of pyrite ranging from about 3 wt-% to about 10 wt-% and/or a level of pyrite ranging from about 1 wt-% to about 5 wt-%. Beneficially, the natural minerals can release soluble transition metals at low pH which are effective in killing bacteria due to the generation of reactive oxygen species and damage to bacterial membranes.

An antimicrobial clay may also be modified with various substituents to alter the properties of the clay. Non-limiting examples of modifications include modification with organic material, polymers, reducing agents, and various elements such as sodium, iron, silver, or bromide, or by treatment with a strong acid. In some embodiments, an antimicrobial clay of the present disclosure is modified with reducing metal oxides. In preferred alternatives of the embodiments, when an antimicrobial clay is modified with reducing metal oxides, the antimicrobial clay is modified with pyrite. In still other embodiments, the antimicrobial clay is unmodified.

In exemplary embodiments, the clay can also be a synthetic clay that mimics the structure of the clay that provides the antimicrobial efficacy against bacteria.

Additional disclosure of clays is set forth in Unearthing the Antibacterial Activity of a Natural Clay Deposit by Keith Morrison, Arizona State University (December 2015); Catalogued Dissertation Presentation, and https://core.ac.uk/download/pdf/4270172.pdf, each of which are herein incorporated by reference in its entirety.

The particle size of the antimicrobial clay may be an important factor that can affect its effectiveness, as well as bioavailability, blend uniformity, segregation, and flow properties. In general, smaller particle sizes of clay increase its effectiveness by increasing the surface area. In some embodiments, the particle size of the clay is reduced through processes such as milling. In an embodiment, milling can be used to reduce the particle size of clay down to about 10 microns.

In various embodiments, the average particle size of the clay is less than about 100 microns in diameter, or less than about 90 microns in diameter, or less than about 80 microns in diameter, or less than about 70 microns in diameter, or less than about 60 microns in diameter, or less than about 50 microns in diameter. In some applications, the average particle size of the clay is between about 10-100 microns in diameter, or preferably between about 10-50 microns in diameter, or still more preferably between about 10-25 microns in diameter. Without being limited to a particular mechanism of processing the clay for the compositions described herein, the clay particles pass through a mesh screen to achieve a uniform desired micron size, as is referred to as clay milling. As opposed to conventional use of a metal ball to aid in the milling, the compositions described herein are produced using a ceramic ball to ensure no metal contaminants are included in the clay delivery systems.

The clay is preferably free of metal contaminants. The clay is further free of lead and other metals. In some embodiments, the clay is preferably sterilized before formulation into the clay delivery system to kill any environmental microbes in the clay. Similarly, in embodiments wherein a reducing agent may be added to an antimicrobial clay, the particle size of a reducing agent may also be an important factor that can affect its effectiveness, and in general, smaller particle sizes increase its effectiveness. Preferably, the average particle size of the reducing agent that may be added to an antimicrobial clay is less than 1 micron in size.

In some embodiments, the clay is included in the clay delivery system in an amount of at least about 10 wt-% to about 50 wt-%, about 15 wt-% to about 40 wt-%, or about 20 wt-% to about 35 wt-%. In addition, without being limited according to the invention, all ranges recited are inclusive of the numbers defining the range and include each integer within the defined range. Beneficially, the compositions described herein utilizing the at least one nonionic block EO-PO copolymer are able to formulate large amounts of clay, including at least about 10 wt-%, 15 wt-%, preferably at least about 20 wt-%, 25 wt-%, and still more preferably at least about 30 wt-% in the first part of the delivery system.

The clay delivery systems and compositions of the invention further provide for shelf stable compositions for various applications of use, including topical applications. In embodiments, the clay delivery systems and compositions are shelf stable for a period of at least about 1 year prior to administration. In other embodiments, the clay delivery systems and compositions are stable for a period of at least about 1 year and 6 months (i.e. 36 months) prior to administration. In further embodiments, the clay delivery systems and compositions are stable for a period of time that is longer than about 1.5 years, or 2 years.

Pharmaceutical Compositions

According to embodiments, the clay delivery systems can be incorporated into or serve as the delivery vehicle for a pharmaceutical composition. Exemplary pharmaceutical compositions include the clay delivery system, an additional therapeutic agent and/or additional additives.

Therapeutic Agents

Pharmaceutical compositions incorporating the clay delivery systems include at least one additional therapeutic agent. The at least one additional therapeutic agent is incorporated into the clay delivery system. In some aspects, the clay delivery system serves as a delivery vehicle for the therapeutic agent for delivery to the target organ. In other aspects, the clay delivery system enhances the therapeutic properties of the therapeutic agent.

In an embodiment, the therapeutic agent is hydroxytyrosol. In another embodiment, the therapeutic agent is oleuropein. In a still further embodiment, the therapeutic agent is hydroxytyrosol in combination with oleuropein.

In an embodiment, the therapeutic agents used herein encompasses any formulation or composition that includes hydroxytyrosol, including but not limited to, hydroxytyrosol alone, hydroxytyrosol in combination with oleuropein, undiluted or at any dilution where an effective amount of hydroxytyrosol is present. Exemplary compositions containing hydroxytyrosol and oleuropein are commercially available under the tradename Olivamine® (available from McCord Research Inc.), such as those disclosed in U.S. Pat. No. 8,809,311, which is herein incorporated by reference in its entirety. Olivamine® combines olive polyphenol, hydroxytyrosol, with specific vitamins and amino acids that play vital roles in the cellular antioxidant response system, amplifying the antioxidant properties of hydroxytyrosol (Olivamine®: 20 µM hydroxytyrosol, 80 µM oleuropein, 2 mM N-acetylcysteine, 50 µM L-proline, 2 mM glycine and 100 µM taurine).

In one aspect, hydroxytyrosol compositions include any hydroxytyrosol-based inhibitor of the LDS1 protein. Suitable hydroxytyrosol-based inhibitor of the LDS1 protein include, for example, hydroxytyrosol, a hydroxytyrosol derived compound, a hydroxytyrosol substituted compound, a hydroxytyrosol metabolite (originating from a prodrug), and combinations of the same.

The therapeutic agents according to the invention employ hydroxytyrosol. Hydroxytyrosol (HT; CAS Registry number [10597-60-1]), is also known as 3-hydroxytyrosol, 3,4-dihydroxyphenyl ethanol (DOPET) or 4-(2-hydroxyethyl)-1,2-benzenediol. Hydroxytyrosol has the Formula I set out below:

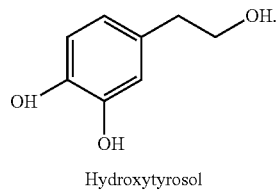

Hydroxytyrosol — Formula I

For use in the hydroxytyrosol-containing formulations and other compositions of the present invention, hydroxytyrosol may be derived from natural sources or prepared by chemical synthesis. For example, the hydroxytyrosol may be obtained as an extract of, or otherwise derived from, olive leaves, olive fruits and vegetation water of olive oil production. When obtained as an extract, for example, of olive leaves, the extract will contain hydroxytyrosol, tyrosol, oleuropein, and other polyphenols. In one preferred embodiment, the hydroxytyrosol is obtained as an olive leaf extract of *Olea europaea*. Further description regarding the isolation and purification of hydroxytyrosol from olive by-products is described by Fernandez-Bolanos et al., Cur. Org. Chem. 12: 442-463 (2008), which is hereby incorporated by reference in its entirety.

In addition to isolated, purified, derived and/or synthesized hydroxytyrosol compositions, according to a further embodiment, a hydroxytyrosol derivative and/or substituted hydroxytyrosol, include for example hydroxytyrosol acyl derivatives according to the following Formula II:

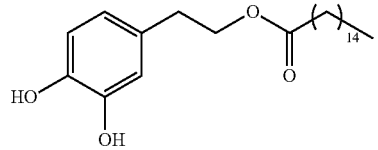

Hydroxytyrosol acyl derivatives. — Formula II

Further reaction and/or substitution of the acyl derivative can include use of various acylating agents, including for example, palmitic acid, ethyl butyrate, ethyl stearate, ethyl oleato, ethyl eicosapentaenoate, ethyl docosahexaenoate to produce various fatty acid esters of hydroxytyrosol. Exemplary acyl derivatives include those shown in Table 3 of Fernandez-Bolanos et al., Cur. Org. Chem. 12: 442-463 (2008), which is reproduced below.

TABLE 3

| Acylating Agents | Product |
| --- | --- |
| Palmitic acid | 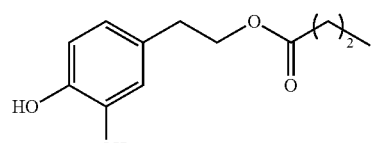 46 |
| Ethyl butyrate | 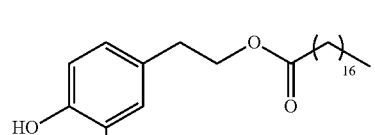 47 |
| Ethyl stearate | 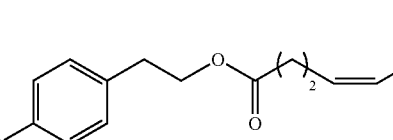 48 |
| Ethyl oleato | 41 |

TABLE 3-continued

| Acylating Agents | Product |
|---|---|
| Ethyl eicosapentaenoate | 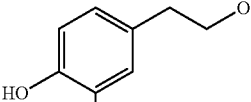<br>49 |
| Ethyl docosahexasenoate | 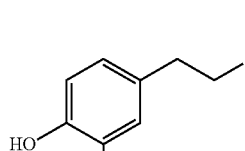<br>50 |

In a further embodiment, compounds derived from hydroxytyrosol (hydroxytyrosol derivatives), hydroxytyrosol substituted compound, metabolites of hydroxytyrosol (its derivatives and/or substituted compounds), one or more mixtures thereof, or one or more combinations thereof are employed for hydroxytyrosol compositions.

In a further embodiment, hydroxytyrosol derivative and/or substituted hydroxytyrosol, include for example hydroxytyrosol acyl derivatives, substitute'd hydroxyl groups and/or substituted compositions are employed and have the following general Formula III:

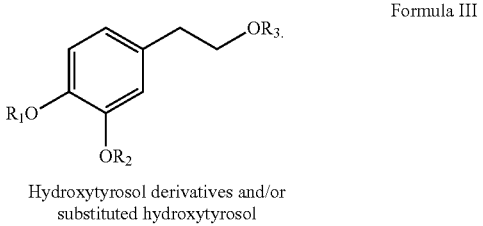

Formula III

Hydroxytyrosol derivatives and/or substituted hydroxytyrosol wherein R1, R2, and R3 provide a pharmaceutically acceptable salt, solvate, prodrug and/or isomer of hydroxytyrosol that has inhibitory efficacy against the LSD1 protein; interacts with Trp807, Phe560, and/or His812 of LSD1; improves cell viability in normal, non-cancer cells; abrogates or prevents chemotherapy-induced dysfunction; abrogates or prevents high glucose-induced dysfunction; increases antioxidant activity; and/or induces or enhances angiogenesis.

In a still further embodiment, hydroxytyrosol derivative and/or substituted hydroxytyrosol, include for example hydroxytyrosol acyl derivatives, substituted hydroxyl groups and/or substituted compositions are employed and have the following general structure:

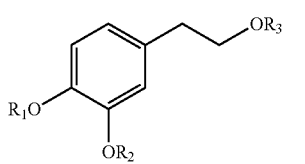

wherein R1, R2 and R3 are independently selected from the group consisting of hydrogen, substituted or unsubstituted alkyl, substituted or unsubstituted alkenyl, substituted or unsubstituted alkynyl, substituted or unsubstituted aryl, substituted or unsubstituted heterocyclyl, substituted or unsubstituted acyl, ORa, SRa, SORa, SO2Ra, OSO2Ra, OSO3Ra, NO2, NHRa, N(Ra)2, =N—Ra, N(Ra)CORa, N(CORa)2, N(Ra)SO2R', N(Ra)C(=NRa)N(Ra)Ra, CN, halogen, CORa, COORa, OCORa, OCOORa, OCONHRa, OCON(Ra)2, CONHRa, CON(Ra)2, CON(Ra)ORa, CON(Ra)SO2Ra, PO(ORa)2, PO(ORa)Ra, PO(ORa)(N(Ra)Ra) and aminoacid ester having inhibitory efficacy against the LSD1 protein; and further wherein each of the Ra groups is independently selected from the group consisting of hydrogen, substituted or unsubstituted alkyl, substituted or unsubstituted alkenyl, substituted or unsubstituted alkynyl, substituted or unsubstituted aryl, and substituted or unsubstituted heterocyclyl, substituted or unsubstituted acyl, and the like having inhibitory efficacy against the LSD1 protein; and further wherein each of the substituted or unsubstituted alkyl, alkenyl, alkynyl, aryl, heterocyclyl, and/or acyl groups are C1-28 (including all ranges therein).

In a preferred embodiment, the therapeutic agents further comprise oleuropein and have the following general Formula IV:

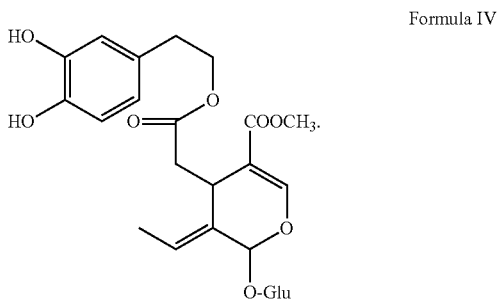

Formula IV

Oleuropein

In a preferred embodiment, the therapeutic agents further comprise L-sulforphane. Sulforaphane is a compound within the isothiocyanate group of organosulfur compounds. In a further preferred embodiment, the therapeutic agents further comprise curcumin, a natural compound produced by *Cur-*

*cuma longa* plants. Curcumin is the primary curcuminoid of turmeric, a member of the ginger family.

In a preferred embodiment, the therapeutic agents further comprise N-acetyl cysteine. In another preferred embodiment, the composition further comprises hydroxytyrosol, N-acetyl cysteine and an additional component having a molecular weight not in excess of 500 Daltons that improves the health or viability of skin cells. Such additional components, for example, may include other antioxidants, vitamins (e.g. Vitamins A, B, D, C and/or E, in all forms), minerals, and/or amino acids. Non-limiting examples of other antioxidants include ascorbic acid (vitamin C) and its salts, ascorbyl esters of fatty acids, ascorbic acid derivatives (e.g., magnesium ascorbyl phosphate, sodium ascorbyl phosphate, and ascorbyl sorbate), EGCG, oleuropein, tocopherol (vitamin E), tocopherol sorbate, tocopherol acetate, other esters of tocopherol, tyrosol, butylated hydroxy benzoic acids and their salts, gallic acid and its alkyl esters such as propyl gallate, uric acid and its salts and alkyl esters, sorbic acid and its salts, lipoic acid, amines (e.g., N,N-diethylhydroxylamine and amino-guanidine), sulfhydryl compounds (e.g., glutathione), dihydroxy fumaric acid and it salts, glycine pidolate, arginine pilolate, nordihydroguaiaretic acid, bioflavinoids, curcumin, lyseine, methionine, proline, superoxide dismutase, resveratrol, and other polyphenols. In another embodiment, the composition comprises hydroxytyrosol, N-acetyl cysteine, and one or more of cystine, cystine derivatives, vitamin C, tannic acid, vitamin E, vitamin E derivatives, catechin, niacin, unsaturated fatty acids, vitamin P, vitamin Q, glutathione, isoflavones, guava, selenium, oleuropein or other polyphenol(s). In one embodiment, the composition comprises hydroxytyrosol, N-acetyl cysteine and one or more of glycine, L-taurine, L-proline, niacinamide (vitamin B3), pyridoxine (vitamin B6), and methylsulfonylmethane.

In one embodiment, the composition contains non-amino acid additives such as aloe vera, oat extract, hyaluronic acid, betaglucan or like substance to provide glycosaminoglycans for extracellular matrix protection. Vitamins may be additives, especially vitamins A/D3, all B vitamins and all stable C vitamins. Omega 3 and 6 fatty acids will be balanced with the greater percentage being 3. In one embodiment, the composition may contain other antioxidants, anti-inflammatory agents and tissue repair ingredients known to have wound healing benefits. For example, in one embodiment, the composition contains olive leaf extract, vitamin A/D3, Vitamin C, and essential fatty acids from olive oil, canola oil, safflower oil, borrage oil and sunflower oil. Also, preferably, olive leaf extract is present in the composition of the present invention.

In some embodiments, the therapeutic agents may include additional amino acids, and other functional ingredients may include, for example oleuropein, N-acetyl cysteine, antioxidants, vitamins (e.g. Vitamins A, B, D, C and/or E, in all forms), and/or minerals, L-sulforphane, and curcumin, such as those disclosed in U.S. Patent Application Pub. No. US 2011-0034519 which is herein incorporated by reference in its entirety.

An exemplary preferred formulation includes both hydroxytyrosol (5%) in amounts between about 1-10 wt %, oleuropein (20%) (olive leaf extract) in amounts between about 5-20 wt % in addition with other functional ingredients including N-acetyl cysteine, L-proline, glycine, L-taurine, vitamins (niacinamide, pyridoxine), and methylsulfonylmethane.

Another exemplary preferred formulation includes both hydroxytyrosol (4.5%) in amounts between about 5-25 wt %, oleuropein (10%) (olive leaf extract) in amounts between about 20-70 wt % in addition with other functional ingredients including N-acetyl cysteine, L-proline, glycine, L-taurine, vitamins (niacinamide, pyridoxine), and methylsulfonylmethane.

Antimicrobial Agents

In embodiments, the therapeutic agent is an antimicrobial agent. Representative examples of topical antimicrobial agents include lincosamides (i.e. clindamycin, lincomycin), erythromycin, minocycline, tetracycline, and the pharmaceutically acceptable salts, esters, or prodrugs thereof. Additionally, other antimicrobial agents suitable for use include, amikacin, amikacin sulfate, bacitracin, bacitracin zinc, chlortetracycline hydrochloride, dihydrostreptomycin sulfate, crystalline dihydrostreptomycin sulfate, dihydrostreptomycin hydrochloride, gentamicin sulfate, sterile gentamicin sulfate, kanamycin sulfate, sterile kanamycin sulfate, neomycin sulfate, sterile neomycin sulfate, netilmicin sulfate, oxytetracycline, paromomycin sulfate, polymyxin B, polymyxin B sulfate, sisomicin sulfate, sterile streptomycin sulfate, tobramycin and sterile tobramycin sulfate.

Additional Additives

Pharmaceutical compositions incorporating the clay delivery systems can optionally include additional additives. The additional additives include components conventionally included with pharmaceutical preparations, including for example preparations for topical administration. Examples that may be mentioned are additives which are suitable for producing powders, emulsions, suspensions, aerosols, oils, ointments, fatty ointments, creams, pastes, gels and gel sheets, syrups, foams or solutions, and transdermal therapeutic systems. In other embodiments, additional functional ingredients may be included in the compositions as additional additives. The functional ingredients provide desired properties and functionalities to the compositions, including a material that when combined with a therapeutic agent provides a beneficial property in a particular use or treatment.

In certain embodiments, the formulation includes a solvent. Suitable solvents for use in the formulations of the present invention include, but are not limited to, water, ethanol, butylene glycol, propylene glycol, propanediol, isopropyl alcohol, isoprene glycol, glycerin, Carbowax (polyethylene glycol) 200, Carbowax 400, Carbowax 600, and Carbowax 800. In addition, combinations or mixtures of these solvents may be used according to the present invention. In one particular embodiment, the solvent is water.

Depending on the particular physical dose form, an emulsifier may be included. Suitable emulsifiers for use in the formulations described herein include, but are not limited to, various oils, such as rosemary, olive oil, argon and *eucalyptus*, Incroquat Behenyl TMS (behentrimonium methosulfate, cetearyl alcohol), non-ionic emulsifiers like polyoxyethylene oleyl ether, PEG-40 stearate, ceteareth-12 (e.g., Eumulgin B-1 manufactured by Henkel), ceteareth-20 (e.g., Eumulgin B-2 manufactured by Henkel), ceteareth-30, Lanette O (manufactured by Henkel; ceteareth alcohol), glyceryl stearate (e.g., Cutina GMS manufactured by Henkel), PEG-100 stearate, Arlacel 165 (glyceryl stearate and PEG-100 stearate), steareth-2 and steareth-20, or combinations/mixtures thereof, as well as cationic emulsifiers like stearamidopropyl dimethylamine and behentrimonium methosulfate, or combinations/mixtures thereof. In addition, cationic emulsifiers may be combined or mixed with non-ionic emulsifiers.

Suitable viscosity adjusting agents (i.e., thickening and thinning agents) for the formulations described herein include, but are not limited to, protective colloids or nonionic gums such as carrageenan, hydroxyethylcellulose (e.g., Cellosize HEC QP52,000-H, manufactured by Amerchol), xanthan gum, and *sclerotium* gum (Amigel 1.0), as well as magnesium aluminum silicate (Veegum Ultra), silica, microcrystalline wax, beeswax, paraffin, and cetyl palmitate. In addition, appropriate combinations or mixtures of these viscosity adjusters may be utilized.

Suitable surfactants for use in the formulations of the present invention include, but are not limited to, nonionic surfactants like Surfactant 190 (dimethicone copolyol), Polysorbate 20 (Tween 20), Polysorbate 40 (Tween 40), Polysorbate 60 (Tween 60), Polysorbate 80 (Tween 80), lauramide DEA, cocamide DEA, and cocamide MEA, amphoteric surfactants like oleyl betaine and cocamidopropyl betaine (Velvetex BK-35), and cationic surfactants like Phospholipid PTC (Cocamidopropyl phosphatidyl PG-dimonium chloride). Combinations of surfactants may also be employed.

The formulations may also include one or more preservatives. Suitable preservatives include, but are not limited to, anti-microbials such as Lincoserve BDP, Germaben II (manufactured by ICI; propylene glycol, diazolidinyl urea, methylparaben, and propylparaben), methylparaben, propylparaben, imidazolidinyl urea, benzyl alcohol, sorbic acid, benzoic acid, sodium benzoate, dichlorobenzyl alcohol, phenoxyethenol, dehydroacetic acid, and formaldehyde, as well as physical stabilizers and anti-oxidants such as alpha-tocopherol (vitamin E), sodium ascorbate/ascorbic acid, ascorbyl palmitate and propyl gallate. In addition, combinations or mixtures of these preservatives may also be used.

Various additives, known to those skilled in the art, may also be included in the formulations. In certain embodiments, for example, it may be desirable to include one or more skin permeation enhancers in the formulation. Examples of suitable enhancers include, but are not limited to, ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184, P85, P105, P338), Tween (20, 40, 60, 80), and lecithin (U.S. Pat. No. 4,783,450); alcohols such as ethanol, propanol, octanol, benzyl alcohol, and the like; polyethylene glycol and esters thereof such as polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine, and triethanolamine; terpenes; alkanones; and organic acids, particularly citric acid and succinic acid. Azone® and sulfoxides such as DMSO and C10 MSO may also be used.

Other enhancers are those lipophilic co-enhancers typically referred to as "plasticizing" enhancers, i.e., enhancers that have a molecular weight in the range of about 150 to 1000, and an aqueous solubility of less than about 1 wt. %. Lipophilic enhancers include fatty esters, fatty alcohols, and fatty ethers. Examples of specific fatty acid esters include methyl laurate, ethyl oleate, propylene glycol monolaurate, propylene glycerol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, e.g., a C2-C4 alkane diol or triol, is substituted with one or two fatty ether substituents.

Additional permeation enhancers will be known to those of ordinary skill in the art of drug delivery, and/or are described in the pertinent texts and literature. See, e.g., Percutaneous Penetration Enhancers, eds. Smith et al. (CRC Press, 1995).

The formulations may also comprise one or more moisturizers. Suitable moisturizers for use in the formulations of the present disclosure include, but are not limited to, lactic acid and other hydroxy acids and their salts, glycerin, propylene glycol, butylene glycol, sodium PCA, Carbowax 200, Carbowax 400, and Carbowax 800. Suitable emollients for use in the formulations described herein include, but are not limited to, PPG-15 stearyl ether, lanolin alcohol, lanolin, lanolin derivatives, cholesterol, propanediol, isostearyl neopentanoate, octyl stearate, mineral oil and various other oils, such as rosemary, olive oil, argon and *eucalyptus*, isocetyl stearate, Ceraphyl 424 (myristyl myristate), octyl dodecanol, dimethicone (Dow Corning 200-100 cps), phenyl trimethicone (Dow Corning 556), Dow Corning 1401 (cyclomethicone and dimethiconol), and cyclomethicone (Dow Corning 344), and Miglyol 840 (manufactured by Huls; propylene glycol dicaprylate/dicaprate). In addition, appropriate combinations and mixtures of any of these moisturizing agents and emollients may be used in accordance with the present invention.

Suitable fragrances and colors, such as FD&C Red No. 40 and FD&C Yellow No. 5, may also be used in the formulations.

Other suitable additional and adjunct ingredients which may be included in the formulations of the present invention include, but are not limited to, abrasives, absorbents, anti-caking agents, anti-foaming agents, anti-static agents, astringents (e.g., witch hazel, alcohol, and herbal extracts such as chamomile extract), binders/excipients, buffering agents, chelating agents (e.g., Versene EDTA), film forming agents, conditioning agents, opacifying agents, pH adjusters (e.g., citric acid and sodium hydroxide), and protectants. Examples of each of these ingredients, as well as examples of other suitable ingredients in product formulations, may be found in publications by The Cosmetic, Toiletry, and Fragrance Association (CTFA). See, e.g., CTFA Cosmetic Ingredient Handbook, 2nd edition, eds. John A. Wenninger and G. N. McEwen, Jr. (CTFA, 1992).

The formulations may also contain irritation-mitigating additives to minimize or eliminate the possibility of skin irritation or skin damage resulting from the pharmacologically active base or other components of the composition. Suitable irritation-mitigating additives include, for example: alpha-tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; N acetyl cysteine; cis-urocanic acid; capsaicin; L-sulforphane; Curcumin; and chloroquine. The irritant-mitigating additive, if present, may be incorporated into the present formulations at a concentration effective to mitigate irritation or skin damage.

Methods for Delivering a 'Bedside Ready' Clay Composition for Various Applications of Use In an aspect, methods of delivering a clay composition for various applications are provided, including topical applications. The methods include combining the first part system and the second part system of the two-part clay delivery system. In embodiments, the first part comprises clay, suspending agent(s), a nonionic block EO-PO copolymer, and a gellant, and the second part comprises at least one nonionic block EO-PO copolymer in a water-based system. The clay is present in the first part of the two-part delivery system to prevent premature activation of the clay from hydration by the water-based system in the second part of the two-part delivery system. The methods further comprise acceleration of the release of clay into the water-based system of the second part, facilitated by the nonionic block EO-PO copolymer in the first part. The contacting of the clay to the water-based system activates the antimicrobial properties of the clay, where delivery of the clay is enhanced by the at least one nonionic block EO-PO copolymer(s) in the second part.

In embodiments, the clay can be sterilized before formulation into the clay delivery system. In embodiments the clay is sterilized by autoclaving or dry heat. Autoclaving uses a heated container to apply high heat and pressure to provide steam sterilization of a surface or substrate. In an exemplary method, the clay can be autoclaved at least about 1 hour at a temperature above about 100° C., 105° C., 110° C., 115° C., 120° C., or above and at a pressure above about 13 psi, 14 psi, 15 psi, 16 psi, 17 psi, 18 psi, 19 psi, 20 psi, or above. In an exemplary embodiment the clay is autoclaved at a temperature of at least about 120° C. at a pressure of above 17 psi for about 1 hour for sterilization. Although the use of autoclaving clays has been performed by others, it is unique to autoclave the clay as a dry powder for incorporation into the clay compositions as part of the two-part delivery system.

When the clay is hydrated, or once the clay comes in contact with a water source (such as the second part of the delivery system), the clay releases metals, such as iron (particularly reduced $Fe^{2+}$) and aluminum (particularly $Al^{3+}$), where both elements cause toxicity to bacteria through damaging bacterial membranes. The damaging of the membranes then allows for the excess iron to cause intracellular protein damage through oxidation. Hydroxyl radicals are generated as Fe2+ is oxidized by $H_2O_2$ through the Fenton reaction. The proximity of .OH generation to target to be treated (i.e. tissue or organ) is important for toxicity of the pathogen as the radical .OH has a short half-life (estimated at between $10^{-9}$ second half life and also diffuses only nanometers before reacting.

Further, not only does the clay deliver toxins to the targeted bacteria, the clay can also absorb toxins. In embodiments, the clay is used to remove oils, secretions, toxins, and contaminants from a treated surface, such as a tissue or organ of the body.

Further, the nonionic block EO-PO copolymers of the clay delivery system beneficially serve as a delivery vehicle for the antimicrobial compositions and provide various benefits. In particular, when the temperature rises and reaches the critical micelle temperature (CMT) of the nonionic block EO-PO copolymer(s), the copolymers aggregate, forming spherical micelles, with the hydrated PEO units aligning along the outer lining, and the hydrophobic PPO units in the inner core of the micelle. The hydrophobic core of the micelles provides benefits in delivering hydrophobic drugs and other therapeutic agents. Further, in some aspects, the nonionic block EO-PO copolymers are able to prevent or have a reversal effect on multiple drug resistance (MDR) (the ability of microbes to grow even in the presence of chemicals, i.e. therapeutic agents, that would usually inhibit their growth). The nonionic block EO-PO copolymers interact with MDR cells through several different mechanisms, such as those discussed in Chowdhury P. et al., *Pluronic Nanotechnology for Overcoming Drug Resistance*. In: Yan B. et al. (eds) Bioactivity of Engineered Nanoparticles (2017), which is hereby incorporated by reference in its entirety.

The methods described herein preferably employ clay compositions for topical application. The clay compositions are preferably applied to the surface of a tissue or organ of the body, such as the skin, mucosal cells and tissues (e.g., alveolar, buccal, lingual, masticatory, or nasal mucosa, and other tissues and cells that line hollow organs or body cavities) or exposed tissue. In an embodiment, the methods described herein preferably employ clay compositions for application to skin, mucosal cells, intestinal track, ear canal, nasal passages, oral cavities or combinations thereof.

The compositions and methods of the present invention may be used to treat skin that is dry, cracked, scaly, or exhibiting redness or edema but otherwise appears intact to the unaided eye. These symptoms may be presented as a result of an underlying disease or metabolic condition such as diabetes or, alternatively, may be caused by excessive trans-epidermal water loss. Trans-epidermal water loss in excess of about 5 $g/hr/cm^2$ can activate an inflammatory response in the epidermis and dermis. Many factors, such as relative humidity below 40%, changes in skin pH, normal aging and disruption of the stratum corneum contribute to excessive trans-epidermal water loss.

The compositions and methods of the present invention may be used to treat more serious wounds, that is, wounds characterized by a partial or total thickness skin loss, including wounds that are at risk of necrosis. When a wound is characterized by a partial or total thickness skin loss, one of the phases of wound healing is the proliferative phase. The proliferative phase typically includes angiogenesis, collagen deposition, granulation tissue formation, epithelialization, and wound contraction. Wound closure thus requires that cells be in a proliferative phase and it is preferred, therefore, that any composition applied to an open wound not induce the cells in the open wound area into a quiescent state.

The compositions and methods of the present invention may also be used to treat/reduce inflammation. In an embodiment, an exemplary delivery system containing Poloxamer 188, along with therapeutic agents hydroxytyrosol and oleuropein, are suitable for repairing damaged cells and reducing inflammation.

In another embodiment, an exemplary delivery system containing Poloxamer 407, along with therapeutic agents hydroxytyrosol and the oleuropein, are effective against MRSA by causing damage to bacterial cells. In a still further embodiment, delivery systems combining these poloxamers and therapeutic agents can beneficially provide synergistic results in reducing inflammation and/or treating MRSA infections.

In still another embodiment, the clay delivery systems are effective against gastrointestinal pathogens and bacteria, preferably C. *Difficile*. Without being limited to a particular mechanism of action, the clay delivery systems coat a treated surface (such as a tissue or organ of the body) and effectively kill the gastrointestinal bacteria, such as C *Difficile*. The coating provides a local effect on the gastric mucosa, coating it and protecting it from the corrosive effects of acid and pepsin while providing the local antimicrobial properties. C. *Difficile* burdens the health care system with costs of 3.2 billion dollars annually. It is a leading cause of hospital associated gastrointestinal illness and it places the lives of immune compromised patients and the elderly at a higher risk of complications that could lead to death. The current treatment recommendation for patients with mild to moderate C. *Difficile* is metronidazole 500 mg orally three times a day for 10 days. For patients with severe C. *Difficile*, the recommended treatment is vancomycin, 125 mg orally four times a day for 10 days. The risks associated with these recommendations are that often the C. *Difficile* was antibiotic induced. The rates of C. *Difficile* have been rising steadily since 2000. This is especially the case with the elderly confined to hospitals and long-term care facilities. Within this population the risk of C. *Difficile* could be as high as 50%. The two biggest risk factors are exposure to antibiotics and organisms common within the institutional setting. To reduce the risk of C. *Difficile* infection in patient populations the use of the clay delivery systems are administered, including for example, delivery as a syrup prophylactically or at the time of diagnosis through the course of treatment. Beneficially, such treatment provides a low cost method to protect patients and reduce the risks and complications inherent with the infection.

Without being bound to any particular theory and based upon evidence obtained to-date, compositions of the present invention may be used to improve the health and viability of skin cells or other tissues or organs of the body that are diseased or distressed as a result of a metabolic condition. For example, compositions comprising hydroxytyrosol and oleuropein may be used to reduce the concentration of free-radicals in the cells of skin tissue to improve cellular function. In addition, compositions comprising sufficient hydroxytyrosol and oleuropein may be used to induce cells into or maintain them in a reversible quiescent state to provide them with time to heal and return to a more viable state with a reduced risk of necrosis.

Methods for Antimicrobial Treatment Using a Clay Delivery System

Similar to the methods of delivering a clay composition for topical applications, methods of using a clay delivery system for antimicrobial treatment are provided. In an embodiment, the clay delivery systems provide a vehicle for treating microbial infections, including chronic and non-chronic wounds in need of antibacterial treatment. In a further embodiment, the clay delivery systems are particularly well suited for treating wounds with an antibiotic resistant bacterium.

Without being limited to a particular mechanism of action or theory of the invention, clays have adsorption (i.e. attraction of molecules) and absorption (i.e. liquid uptake) qualities. The small particle size (e.g. between 1-100 microns in diameter) allows for the removal of secretions, toxins and contaminants. In particular, bodily fluids like exudate and saliva are pH neutral that work with the release of minerals from the clay. By reducing the pH of these fluids clay makes the tissues a less friendly environment for pathogens, thereby providing at least one mechanism for the efficacy of the clay delivery systems described herein.

The methods include combining the first part system and the second part system of the two-part clay delivery system. In embodiments, the first part comprises clay, suspending agent(s), a nonionic block EO-PO copolymer, and a gellant, and the second part comprises at least one nonionic block EO-PO copolymer in a water-based system. The clay is present in the first part of the two-part delivery system to prevent premature activation of the clay from hydration by the water-based system in the second part of the two-part delivery system. The methods further comprise acceleration of the release of clay into the water system of the second part, facilitated by the nonionic block EO-PO copolymer in the first part. The contacting of the clay to the water-based system activates the antimicrobial properties of the clay, where delivery of the clay is enhanced by the at least one nonionic block EO-PO copolymer(s) in the second part. In other embodiments, an additional therapeutic agent may be combined with the clay delivery system to provide synergistic antimicrobial efficacy.

Activation of the clay results in the release of elements such as iron (particularly reduced $Fe^{2+}$) and aluminum (particularly $Al^{3+}$), where both elements cause toxicity to bacteria through damaging bacterial membranes. The damaging of the membranes then allows for the excess iron to cause intracellular protein damage through oxidation. Further, not only does the clay deliver toxins to the targeted bacteria, the clay can also absorb toxins. In embodiments, the clay is used to remove oils, secretions, toxins, and contaminants from a treated surface, such as a tissue or organ of the body.

Beneficially, the antimicrobial activity of the clay is not activated until the clay is hydrated, or once it comes into contact with water. Once the clay is activated, the antimicrobial activity of the clay lasts for a period of at least about 12 hours, and more preferably, for a period of around 24 hours. The ability to control the release of clay into the water-based system is critical in controlling the activation of the antimicrobial clay, and further controlling the time period for antimicrobial treatment. Such time release profiles of the clay into the water-based system provides numerous benefits for a once a day treatment dose. In embodiments, the methods provide benefits to hospitals and long-term care facilities for only requiring wound care or dressing changes daily. However, in some embodiments where bacterial infections are known to replicate more quickly, more frequent dosing may be preferred. In an exemplary embodiment, when treating MRSA, for example, dosing may be more frequently for an improved kill rate, such as two to four times daily. This will be important to ensure there is a 100% kill rate of the bacteria.

Further, not only does the clay provide antimicrobial activity against bacteria, the nonionic block EO-PO copolymers of the invention further provide beneficial antimicrobial properties. The nonionic block EO-PO copolymer in the first part delivery system, and the at least one nonionic block EO-PO copolymer in the second part delivery system are effective in carrying pharmaceutical compounds, such as additional therapeutic agents, into the bacteria and killing the bacteria via toxicity. In embodiments, this nonionic block EO/PO copolymer is poloxamer 407. Further, a second nonionic block EO-PO copolymer in the water-based system of the second part delivery system repairs cell membranes and reduces inflammation on the target surface being treated. In embodiments, this nonionic block EO-PO copolymer is poloxamer 188. The various capabilities of the nonionic block EO-PO copolymers provide synergistic antimicrobial properties to the clay delivery system.

Still further, it has surprisingly been discovered that a hydroxytyrosol and oleuropein combination provides further benefits for wound healing. The combination of hydroxytyrosol and oleuropein along with additional nutritional supplement components of N-acetyl cysteine, glycine, L-taurine, L-proline and optional additional components provide further improved wound healing through the induction of proliferative cells.

The efficacy according to the methods is effective against a broad range of bacteria, including gram positive and gram negative. Exemplary bacteria include for example, *Clostridium* spp. (including C. *Difficile*), *Chlamydia* spp., *Escherichia* spp., *Staphylococcus* spp., *Klebsiella* spp., *Enterococcus* spp., *Acinetobacter* spp., *Pseudomonas* spp., *Streptococcus* spp., including for example *Escherichia Coli, Staphylococcus aureus*, methicillin-resistant *Staphylococcus* aureus (MRSA), *Staphylococcus epidermidis, Klebsielle Pneumonia* including *Carbapenem Resistant Klebsielle Pneumonia, Enterococcus faecalis, Enterococcus hirae, Acinetobacter baumannii, Pseudomonas aeruginosa, Streptococcus pyogenes, Mycobacterium terrae,* and *Mycobacterium avium.* In addition to bacteria it is understood that viruses, fungi, Mycobacteria, yeast and spores can also be treated by the methods disclosed herein.

Additional listings of bacteria, viruses, parasites and fungi suitable for treatment by the clay delivery system and pharmaceutical compositions employing the same for human pathogens is shown in the following Table 4:

TABLE 4

| Bacterial Pathogen | Virus | Parasite | Fungi |
|---|---|---|---|
| *Bacillus athracis* | Adeno-associated virus | *Acanthamoeba* | *Aspergillus clavatus* |
| *Bacillus cereus* | Aichi virus | *Ancylostoma brazilense* | *Aspergillus flavus* |
| *Bordetella pertussis* | Cosavirus | *Angiostrongylus cantonensis* | *Aspergillus fumigatus* |
| *Borrelia burgdorferi* | Coxsackievirus | *Ascaris lumbricoides* | *Blastomyces dermatitidis* |
| *Borrelia garinii* | Dengue virus | *Balantidium coli* | *Candida albicans* |
| *Borrelia afzelii* | Ebola virus | *Balamuthia mandrillaris* | *Candida auris* |
| *Borrelia recurrents* | Echo virus | *Brugia malayi* | *Candida glabrata* |
| *Brucella abortus* | Epstein-Barr virus | *Capillaria hepatica* | *Candida krusei* |
| *Brucella canis* | Hantaan virus | *Capillaria philippinensis* | *Candida lusitaniae* |
| *Brucella melitensis* | Human papillomavirus | *Cyclospora cayetanensis* | *Candida tropicalis* |
| *Brucella suis* | Hepatitis virus A | *Cystoisospora belli* | *Chaetomium globosum* |
| *Campylobacter jejuni* | Hepatitis virus B | *Diphyllobothrium latum* | *Cladophialphora bantianum* |
| *Chamydia pneumoniae* | Hepatitis virus C | *Drancunculus medinensis* | *Coccidioides immitis* |
| *chlamydia trachomatis* | Hepatitis virus D | *Entamoeba histolytica* | *Coccidioides posadasii* |
| *Chlamydophila psittaci* | Hepatitis virus E | *Fasciola hepatica* | *Conidiobolus coronatus* |
| *Clostridium botulinum* | Human adenovirus | *Giardia intestinalis* | *Conidiobolus incongruus* |
| *Clostridium difficile* | Human astrovirus | *Gnathostoma spinigerum* | *Crytococcus albidus* |
| *Clostridium perfringens* | Human coronavirus | *Leishmania* | *Crytococcus gattii* |
| *Clostridium tetani* | Human cytomegalovirus | *Plasmodium* | *Cryptococcus neoformans* |
| *Corynebacterium diptheriae* | Human enterovirus 68, 70 | *Pseudoterranova decipiens* | *Epidermophyton floccosum* |
| *Enterococcus faecalis* | Human herpesvirus 1 | *Sarcocystis* | *Exophiala dermatidis* |
| *Enterococcus faecium* | Human herpesvirus 2 | *Schistosoma mansoni* | *Exophiala jeanselmei* |
| *Escherichia coli* | Human herpesvirus 6 | *Schistosoma haematobium* | *Fusarium solanum* |
| *Francisella tularensis* | Human herpesvirus 7 | *Schistosoma japonicum* | *Fusarium oxyomorph* |
| *Haemophilus influenzae* | Human herpesvirus 8 | *Taenia saginata* | *Histoplasma capsulatum* |
| *Heliobacter pylori* | Human immunodeficiency virus | *Taenia solium* | *Lacazia loboi* |
| *Legionella pneumophila* | Human papillomavirus 1 | *Toxoplasma* | *Malassezia furfur* |
| *Leptospira interrogans* | Human papillomavirus 2 | *Trichinella* | *Malassezia pachydermatis* |
| *Leptospira santarosai* | Human papillomavirus 16, 18 | *Trichuris* | *Magnusiomyces capitatus* |
| *Leptospira weilii* | Human parainfluenza | *Trypanosoma brucei* | *Mucor circillenoides* |
| *Leptospira noguchii* | Human respiratory syncytial virus | *Trypanosoma cruzi* | *Mucor mucedo* |
| *Listeria monocytogenes* | Human rhinovirus | | *Paecilomyces variotti* |

TABLE 4-continued

| Bacterial Pathogen | Virus | Parasite | Fungi |
|---|---|---|---|
| *Mycobacterium leprae* | Human SARS coronavirus | | *Paecilomyces lilacinus* |
| *Mycobacterium tuberculosis* | Human spumaretrovirus | | *Paracoccidioides brasiliensis* |
| *Mycobacterium ulcerans* | Human T-lymphotropic virus | | *Paracoccidioides lutzii* |
| *Mycoplasma pneumoniae* | Human torovirus | | *Penicillium marneffei* |
| *Neisseria gonorrhoeae* | Influenza A virus | | *Pneumocystis jirovecii* |
| *Neisseria meningitis* | Influenza B virus | | *Pseudoallescheria boydii* |
| *Pseudomonas aeruginosa* | Influenza C virus | | *Pseudoterranova decipiens* |
| *Rickettsia rickettsii* | JC polyomavirus | | *Rhizopus oryzae* |
| *Salmonella typhi* | Japanese encephalitis virus | | *Scedosporium anamorphs* |
| *Salmonella typhimurium* | Lassa virus | | *Stachybotrys chartarum* |
| *Shigella sonnei* | Lordsdale virus | | *Trichophyton interdigitale* |
| *Staphylococcus aureus* | Mayaro virus | | *Trichophyton rubrum* |
| *Staphylococcus epidermidis* | MERS coronavirus | | *Tichophyton tonsurans* |
| *Staphylococcus saprophyticus* | Measles virus | | *Trichosporon asachii* |
| *Streptococcus agalactiae* | Merkel cell polyomavirus | | *Trichosporon asteroides* |
| *Streptococcus pneumoniae* | Mumps virus | | *Trichosporon inkin* |
| *Streptococcus pyogenes* | New York virus | | *Trichosporon mucoides* |
| *Treponema pallidum* | Norwalk virus | | |
| *Ureaplasma urealyticum* | Orf virus | | |
| *Vibrio cholerae* | Poliovirus | | |
| *Yersinia pestis* | Rabies virus | | |
| *Yersinia enterocolitica* | Rift valley fever virus | | |
| *Yersinia pseudotuberculosis* | Rosavirus A | | |
| | Ross river virus | | |
| | Rotavirus A | | |
| | Rotavirus B | | |
| | Rotavirus C | | |
| | Rubella virus | | |
| | Salivirus | | |
| | Sapporo virus | | |
| | Semliki forest virus | | |
| | Seoul virus | | |
| | Sindbis virus | | |
| | Southampton virus | | |
| | Tick-borne powassan virus | | |
| | Torque teno virus | | |
| | Toscana virus | | |
| | Vaccinia virus | | |
| | Vesicular stomatitis virus | | |
| | WU polyomavirus | | |
| | West Nile virus | | |
| | Yellow fever virus | | |
| | Zika virus | | |

Additional listings of bacteria, viruses, parasites and fungi suitable for treatment by the clay delivery system and pharmaceutical compositions employing the same for animal pathogens is shown in the following Table 5:

TABLE 5

| Virus | Bacteria | Fungi | Other (Protazoa, mites, worms, parasites, etc.) |
|---|---|---|---|
| African horse sickness virus | Actinomyces spp | Aspergillus spp | Acanthamoeba |
| African swine fever virus | Actinomyces viscosus | Aspergillus flavus | Acanthamoeba castellani |
| Aujeszky's disease virus | Acholeplasma | Aspergillus parasiticus | Acanthamoeba culbertsoni |
| Avian influenza viruses | Anaplasma phagocytophilum | Blastomyces spp | Acanthamoeba |
| Babesia bigemina | Bacillus anthracis | Blastomyces dermatitidis | Aelurostrongylus abstrusus |
| Babesia bovis | Bacteroides spp | Candidia | Ascaris lumbricoides |
| Babesia caballi | Bartonella spp | Coccidioides immitis | Babesia gibsoni |
| Bacillus anthracis | Bartonella quintana | Coccidioides posadasii | Babesia felis |
| Bluetongue virus | Bartonella henselae | Cryptococcus spp | Baylisascaris procyonis |
| Bordetella bronchiseptica | Bordetella bronchiseptica | cryptococcus neoformans | Botfly |
| Borna Disease Virus | Borrelia burgdorferi | cryptococcus neoformans | Capillaria aerophila |
| Bovine leukosis virus | Brucella spp | Fusarium graminearum | Cheyletiella mites |
| Brucella spp | Brucella abortus | Histoplasma capsulatum | Coccidia |
| Brucella abortus | Brucella melitensis | Malassezia spp | Hepatozoon |
| Brucella melitensis | Brucella suis | Malassezia pachydermatis | Isospora felis |
| Brucella ovis | Burkholderia mallei (Pseudomonas mallei) | Micosporum canis | Isospora rivolta |
| Brucella suis | Burkholderia pseudomallei (Pseudomonas pseudomallei) | Microsporum gypseum | Sarcocystis neurona |
| Burkholderia mallei | Campylobacter spp | Mycosporum equinum | Toxoplasma gondii |
| Canine adenovirus | Chlamydia psittaci (Chlamydophila psittaci) | Penicillium puberulum | Cryptosporidium |
| Canine parainfluenza | Clostridium spp | Pneumocystis carnii | Cuterebra larva |
| Canine coronavirus | Clostridium argentinense | Pythium insidiosum | Cytauxzoon felis |
| Canine distemper | Clostridium baratii, | Rhinosporidium seeberi | Demodex canis |
| Canine herpes virus | Clostridium botulinum | Sporothrix schenckii | Demodex catis |
| Canine hepatitis | Clostridium butyricum | Tichophyton spp | Demodex gatoi |
| Canine influenza | Clostridium difficile | Tichophyton equinum | Dirofilaria immitis |
| Canine oral papillomavirus | Clostridium perfringens | Tichophyton mentagrohytes | Encephalitozoon cuniculi |
| Canine parvovirus | Clostridium pilformis | Tichophyton mentagrohytes | Felicola subrostrata |
| Classical swine fever virus | Clostridium tetani | Tichophyton verrucosum | Fleas |
| Cochliomyia hominivorax | Corynebacterium pseudotuberculosis | | Giardia |
| Equine encephalomyelitis viruses | Corynebactrerum spp | | Heterobilharzia americanum |
| Equine herpesvirus | Coxiella burnetii | | Hookworms |
| Equine influenza | Dermatophilus congolensis | | Ancylostoma ceylanicum |
| Echinococcus multilocularis | Ehrlichia canis | | Ancylostoma tubaeforme |
| Echincoccus granulosus | Ehrlichia lewinii | | Leishmania |
| Ehrlichia ruminantium | Enterobacter spp | | Linognathus setosus |

TABLE 5-continued

| Virus | Bacteria | Fungi | Other (Protazoa, mites, worms, parasites, etc.) |
|---|---|---|---|
| Equine infectious anaemia virus | Escherichia coli | | Microsporum canis |
| Feline astrovirus | Francisella tularensis | | Microsporum gypseum |
| Feline Calicivirus (FCV) | Fusobacgterium spp | | Neospora caninum |
| Feline Coronavirus spp | Helicobacter spp | | Ollulanus tricuspis |
| Feline Distemper (FPV) | Helicobacter felis | | Opisthorchis felineus |
| Feline Enteric Coronavirus (FIP) | Helicobacter heilmannii | | Otodecetes cynotis |
| Feline foamy virus (FeFV | Helicobacter pylori | | Physaloptera spp |
| Feline Herpes (FVR) | Helicobacter rappini | | Roundworms |
| Feline Herpesvirus 1 (FHV-1) | Helicobacter salomonis | | Sarcoptes scabiei |
| Feline Immunodeficiency Virus (FIV) | Klebsiella | | Strongyloides stercoralis |
| Feline Leukemia (FeLV) | Lawsonia intracellularis | | Strongyloides tumefaciens |
| Foot and mouth disease virus | Leptospira spp | | Tapeworms |
| Goat pox virus | Leptospira grippotyphosa | | Taenia crassiceps |
| Hendra disease virus | Leptospira interrogans | | Ticks |
| Histoplasma farciminosum | Leptospira Pomona | | Trichinella spiralis |
| Influenza H1N1 | Moraxella | | Trichodectes canis |
| | Mycobacterium spp | | Trichophyton mentagrophytes |
| Japanese encephalitis virus | Mycoplasma canis | | Trichuris campanula |
| Kennel cough | Mycoplasma capricolum subspecies capripneumoniae | | Trichuris serrata |
| Leptospirosis | Mycoplasma haemofelis | | Trichuris vulpis |
| Lumpy skin disease virus | Mycoplasma haemominutum | | Trypanosoma cruzi |
| Lyssa virus | Mycoplasma maculosum | | |
| Morbillivirus spp | Mycoplasma mycoides subspecies mycoides SC | | |
| Mycoplasma spp | Mycoplasma spumans | | |
| Mycoplasma agalactiae | Nocardia asteroides | | |
| Mycoplasma capricolum subspecies capripneumoniae | Nocardia brasiliensis | | |
| Mycoplasma mycoides subspecies mycoides SC and mycoides LC variants | | | |
| Mycoplasma mycoides var capri | Pasteurella multocida | | |
| Avian paramyxovirus type 1) viruses | peptostreptococcus | | |
| Nipah disease virus | Proactinomyces spp | | |
| Orthopoxvirus | Proteus | | |
| Papillomavirus | Pseudomonas spp | | |
| Paramixovirus | Pseudomonas aeruginosa | | |

TABLE 5-continued

| Virus | Bacteria | Fungi | Other (Protazoa, mites, worms, parasites, etc.) |
|---|---|---|---|
| Parvovirus | Rickettsia prowazekii | | |
| Peste des petits ruminants virus | Rickettsia rickettsii | | |
| Phocine spp | Salmonella enterica subspecies enterica serovar Typhi (Salmonella typhi) | | |
| Porcine enterovirus type 9 | Shiga toxin producing Escherichia coli (STEC) | | |
| Porcine herpes virus | Shigella dysenteriae | | |
| Porcine Reproductive and Respiratory Syndrome virus (genotype 2) | Staphylococcus spp | | |
| Potomac Horse Fever | Staphylococcus schleiferi | | |
| Rabies virus and all viruses of the genus Lyssavirus | Staphylococcus aureus | | |
| Reovirus | Staphylococcus intermedius | | |
| Rift Valley Fever virus | Staphylococcus pseudintermedius | | |
| Rinderpest virus | Staphylococcus sciuri | | |
| Rotavirus | Streptococcus spp | | |
| Sheep pox virus | beta-hemolytic Streptococci | | |
| St Louis equine encephalomyelitis virus | Streptococcus equi | | |
| Suid herpesvirus 1 | Streptococcus zooepidemicus | | |
| Swine fever virus | t-mycoplasma | | |
| Swine vesicular disease virus | Taylorella equigenitalis | | |
| Teschen disease virus | ureaplasma | | |
| Theileria annulata | Vibrio cholerae | | |
| Theileria parva | Yersinia pestis | | |
| Trichinella spiralis | | | |
| Trypanosom spp | | | |
| Trypanosom vivax | | | |
| Trypanosom congolense | | | |
| Trypanosom equiperdum | | | |
| Trypanosom evansi | | | |
| Trypanosom simiae | | | |
| Trypanosoma brucei | | | |
| Venezuelan equine encephalomyelitis virus | | | |
| Vesicular stomatitis virus | | | |
| Vesicular stomatitis virus | | | |
| West Nile virus | | | |

The dose regimen will depend on a number of factors that may readily be determined, such as severity of the affected region and responsiveness of the condition to be treated, but will normally be one or more doses per day, with a course of treatment lasting from a single day, to several days, to several months, or until a cure is effected or a diminution of disease state is achieved. In some embodiments, daily or more than one dose per day for at least 4 days, 5 days, 6 days, 7 days, 10 days, 14 days, 21 days, 30 days or greater are provided as a course of treatment. One of ordinary skill may readily determine optimum dosages, dosing methodologies, and repetition rates. In general, it is contemplated that the formulation will be applied as a single treatment. In other embodiments, the formulation will be applied one to four times daily.

Beneficially, the clay composition provides an effective antimicrobial reduction of microbial populations on the treated surface, such as the tissue or organ of the body treated. The activity can be measured by calculating the log reduction in number of microorganisms. In an embodiment, a 99.99% log reduction of microbial populations on the tissue or organ of the body is achieved after 24 hour contact. In an embodiment, at least a 2 log reduction, at least a 3 log reduction, or preferably at least a 4 log reduction of microbial populations on the tissue or organ of the body is achieved after 24 hour contact.

Antimicrobial efficacy of the clay delivery systems can be shown through various quantifiable measurements, including use of time-kill curve study for determining the rate at which antibiotics kill bacteria (in vitro studies) to demonstrate bactericidal activity in drug development; serum bactericidal tests (SBTs) using a patient's serum to determine the effectiveness of an antibiotic (or other therapeutic) (in vitro studies); in vivo studies (e.g. with mice) employing the thigh infection model in neutropenic (to eliminate the effect of immune response) mice.

At least the following phases of evaluations of the clay delivery systems with various actives are to be conducted:

Phase 1 Investigations—formulation quality:

1. Formulation analysis to maximize incorporation of bioactive compounds (e.g. Olivamine, antifungal, and/or antibiotic);

2. Release of and of bioactive compounds from formulation in aqueous solutions HPLC analysis against standard curves for each bioactive compound of interest; calculations of efficiency of reactions and final yields; and/or 3. Retention of activity of bioactive compounds, including: (a) Comparison of antimicrobial activity of starting material and following formulation (and release of relevant compounds). (b) Retention of antioxidant capacity of Olivamine formulations. Kit-based assays for total antioxidant capacity.

Phase 2 Investigations—effects in cell culture (identification of anti-oxidant, anti-inflammatory effects, and any potential cytotoxic effects):

1. Investigation of formulation components (in aqueous phase) in primary human keratinocytes; Ensure there a no keratinolytic effects; explore effects on keratinocyte migration;

2. Investigation of formulation components (in aqueous phase) in primary human fibroblasts (effects on migration and collagen deposition); endothelial cells (ensure angiogenesis—vascular tube formation); and/or 3. Investigation of formulation components (in aqueous phase) in human peripheral blood mononuclear cells; Inflammatory marker release assays (ELISA)—TGF-b, pro-inflammatory interleukin panel.

Phase 3 Investigations—in vivo wound healing experiments and case/or clinical studies:

1. Investigation of best formulations in models of wound healing (excisional and incisional models in non- and diabetic mice); and/or 2. Final formulations in clinical case studies.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Antimicrobial efficacy of the clay delivery systems were evaluated to show that the clay delivery system provides an efficacious two-part, non-activated, amorphous, pH neutral, bedside-ready clay delivery system to treat pathogenic infections in humans and animals. The efficacy testing was designed to assess antimicrobial efficacy at 12, 24 and 48 hours when incubated at room temperature.

A single replicate was evaluated using an inoculum prepared as described. The microorganism tested was *Actinobacter baumannii* ATCC #19606 which was incubated at 32.5±2.5° C. for 3 days, or at the optimum condition required by the organism. Following the incubation period (32.5±2.5° C.), the Tryptic Soy Agar (TSA) slants (TSA with polysorbate 80 and lecithin) were washed with 3.0 mL of sterile saline to harvest bacterial growth. Using a spectrophotometer, adjust the microbial count to approximately $10^8$ organisms per ml. To determine the microorganism concentration of the adjusted suspensions, make 1:10 dilution using sterile PBS. Carry out the dilution to 10-7 dilution. Take 1.0 ml of the $10^{-5}$ to $10^{-7}$ and plate in duplicate onto Tryptic Soy Agar with Lecithin and Tween 80 (TSALT) for bacterial organisms. Incubate at 36±1° C. for 48 hours for bacterial organisms. The number of colonies on each plate were counted and multiplied the average by the reciprocal of the dilution to determine the concentration of the stock culture.

A 90% clay/10% hydrogel mixture (18 grams Clay/2 gram hydrogel) was prepared according to Table 6 and dispensed into a sterile tube. The clay utilized was an Oregon Millard Blue Clay mixture, containing clay minerals smectite, illite, and kaolinite and soluble $Fe^{2+}$ and $Al^{3+}$.

TABLE 6

| Component | Wt-% |
|---|---|
| Clay | |
| Suspending Agent | 51 |
| Nonionic block EO-PO copolymer | 19 |
| Blue Clay | 30 |

TABLE 6-continued

| Component | Wt-% |
|---|---|
| Hydrogel | |
| Water | 87.5 |
| Nonionic block EO-PO copolymer | 10 |
| Additional additives (solvents, viscosity adjustment agents, preservatives) | 2.5 |

20 g or mL of the sample mixture of the two part system was dispensed into a 100 ml sterile flask to provide an approximate $10^5$ to $10^6$ CFU/ml for testing. A dilution series in D/E Neutralizing broth tubes was performed to provide countable plates per time point (1:10, 1:100, and 1:1000), including at time 0, 12, 24 and 48 hours (remainder in flask mixed on a shaker during experiment). For the 1:10 dilution, the sample was prepared sing 1 mL of the clay/hydrogel product and 9 mL DNB, the dilution schemes were continued to 1:100 and 1:1000 dilution levels. A positive control with sterile saline was conducted as well.

The challenge organism was added to diluted product, with each dilution yield to 25-250 colony forming units (CFU)/plate. Each dilution was plated in duplicate. An inoculum was prepared in the same way without the test product. All bacterial plates were incubated at 36±1° C. for 48 to 72 hours. After the incubation period, all plates were counted to achieve final counts per time point accounting for the dilution factor. Plates with no growth are to be reported as <1 multiplied by the dilution factor. For example, if 1:10 dilution was performed, the result will be <10 CFU/g or mL. The log change of bacterial count was calculated and the results are shown in Table 7.

TABLE 7

| | CONCENTRATION OF ORGANISM (CFU/mL) | | | | | |
|---|---|---|---|---|---|---|
| EXPOSURE | | | % REDUCTION | | LOG REDUCTION | |
| TIME | CONTROL | PRODUCT | CONTROL | PRODUCT | CONTROL | PRODUCT |
| Initial | 1.2E5 | 1.2E5 | N/A | N/A | N/A | N/A |
| 0 hr. | 3.6E5 | 3.7E5 | −200.00 | >208.33 | −0.5 | 0.5 |
| 12 hrs. | 1.5E6 | 830 | −1150.00 | 99.31 | −1.1 | 2.2 |
| 24 hrs. | 2.2E6 | <10 | −1733.33 | >99.99 | −1.3 | 4.1 |
| 48 hrs. | 2.1E6 | <10 | −1650.00 | >99.99 | −1.2 | 4.1 |

As shown in the results of Table 7, the clay formulations provided efficacious log reduction of *Actinobacter baumannii*. The testing confirms antimicrobial efficacy at 12, 24 and 48 hours, with greatest log reduction seen at 24+ hours with the log reduction greater than 99.99%. The positive control (no clay delivery system) shows that there was bacteria growth at all time intervals.

These results show efficacy of the two-part clay delivery system without the addition of an additional therapeutic agent to provide antimicrobial efficacy. This demonstrates the clay delivery systems are suitable antimicrobial therapies and can be combined with additional therapeutic agents.

Example 2

Iron and Pyrite ($FeS_2$). Total daily dose should take into consideration the total amount of elemental iron including that contributed from pyrite. Analysis of the clay shows iron content of approximately 32,500 ppm (3.25%).

Oral dosing (elemental iron) considerations:
  <20 mg/kg is non-toxic
  20-60 mg/kg can have toxicity symptoms
  >60 mg/kg can cause severe toxicity, morbidity and mortality
  RDA for Infants & Toddlers: 1 mg/kg between 4th month and 3rd year of life, not to exceed 15 mg/day in infants
Topical dosing as disclosed in U.S. Pat. No. 8,996,104, there is highly variable absorption based on salt forms, oxidative state, skin condition, and formulation. Acceptable transdermal
dosing ranges between about 10 mg-1,000 mg of elemental iron to provide therapeutic benefits.

Aluminum. Analysis of the clay shows aluminum content of approximately 52,000 ppm (5.20%).
  Oral Dosing: From US-DHHS Agency for Toxic Substances and Disease Registry (ATSDR): Minimal risk level (MRL) of 1 mg/kg/day for intermediate (15-364 days) and chronic ingestion (>365 days). There is no MRL provided for acute use.

Accepted safe oral dosing in current antacid products allows for approximately 1,000 mg elemental aluminum daily for a maximum of 2 weeks. There is only limited data suggestion any toxicity issues related to excessive aluminum consumption, but what data does exist has been predominantly seen in industrial settings involving mining, smelting, and refining of aluminum where employees are exposed to fine particulate dust on a daily basis. The symptoms from excessive chronic aluminum exposure appear to be related to disruptions in phosphate, magnesium, calcium, and fluoride absorption/homeostasis/metabolism and not related to direct biological effect or bioaccumulation of aluminum, as disclosed in Rondeau V. A review of epidemiologic studies on aluminum and silica in relation to Alzheimer's disease and associated disorders. Rev Environ Health. 2002; 17(2):107-121.
  Topical Dosing: Current research has found no significant correlation in topical application of aluminum containing products and hypothesized side effects or long term health consequences. Data suggests that outside of industrial settings there is little concern of aluminum toxicity from oral ingestion or topical administration.
Dosing Guidelines:
  Assuming a maximum application of 15 grams per day of a product with 30% blue clay, that would provide approximately 146 mg of elemental iron and 234 mg of elemental aluminum.
  Table 8 shows that even using 30 grams a day of a 60% clay product only provides 585 mg of elemental iron and 936 mg of elemental aluminum—both within the anticipated safe bounds described above.

TABLE 7

Iron Content 3.25%
Content 5.20%

| Daily Dose of Product (grams) | | Total daily dose (elemental) (mg) | | | | | |
|---|---|---|---|---|---|---|---|
| | | 10% Clay | 20% Clay | 30% Clay | 40% Clay | 50% Clay | 60% Clay |
| 5 | Iron | 16.25 | 32.50 | 48.75 | 65.00 | 81.25 | 97.50 |
| | Aluminum | 26.00 | 52.00 | 78.00 | 104.00 | 130.00 | 156.00 |
| 10 | Iron | 32.50 | 65.00 | 97.50 | 130.00 | 162.50 | 195.00 |
| | Aluminum | 52.00 | 104.00 | 156.00 | 208.00 | 260.00 | 312.00 |
| 15 | Iron | 48.75 | 97.50 | 146.25 | 195.00 | 243.75 | 292.50 |
| | Aluminum | 78.00 | 156.00 | 234.00 | 312.00 | 390.00 | 468.00 |
| 20 | Iron | 65.00 | 130.00 | 195.00 | 260.00 | 325.00 | 390.00 |
| | Aluminum | 104.00 | 208.00 | 312.00 | 416.00 | 520.00 | 624.00 |
| 25 | Iron | 81.25 | 162.50 | 243.75 | 325.00 | 406.25 | 487.50 |
| | Aluminum | 130.00 | 260.00 | 390.00 | 520.00 | 650.00 | 780.00 |
| 30 | Iron | 97.50 | 195.00 | 292.50 | 390.00 | 487.50 | 585.00 |
| | Aluminum | 156.00 | 312.00 | 468.00 | 624.00 | 780.00 | 936.00 |

Example 3

Research conducted to determine the effectiveness of clay, within the research setting, does not translate to the bedside. Researchers have tested clay's effectiveness by measuring clay powder into a medium, usually deionized (DI) water, and mixing for a set period of time. This method is not applicable for usage by patient populations; it would notably violate workplace safety guidelines and would not be allowed within the institutional setting due to inhalation and fire risks.

Health risk assessments in the workplace are designed to identify potential health risks associated with products, equipment and the hospital environment. Among the identified health risks powder exposure is thought to be considerable risk factor for workers and patients. Of importance to this art, the micron size associated with hazardous particle inhalation has been established. The inhalable fraction of powders of 100 microns or greater is approximated to be 50%. However, powders of 18 microns or less are known to fully penetrate deep into the lungs. Since the average resolution of the human eye is 100 microns, it is expected that workers exposed to free-clay particles would not anticipate the risk since clay particles are in the 10-100 micron range, preferably from about 10-25 microns. Beneficially, use of the clay delivery systems overcome these risks commonly associated with inhalation of dusts or powders, such as clay powders, by providing a delivery system that does not have inhalable powders.

Inhalation of powder is known to cause respiratory tract damage and may lead to chronic lung disease. The following tolerances for powder use, of any kind, were established by Birmingham Hospital in the UK and serve as a template for institutional safety. The Workplace Exposure Limits (WEL) for dusts or powders: Inhalable, 10 mg/meter$^3$, 8 hour time weighted average (TWA); Respirable, 4 mg/meter$^3$, 8 hour TWA. For shorter exposures these figures should be multiplied by three. Beneficially, use of the clay delivery systems overcome these risks commonly associated with inhalation of dusts or powders, such as clay powders.

Fire hazards are also of primary concern. Hospitals can be oxygen-rich especially in the hyperbaric setting or with patients receiving oxygen treatments. The reactivity of powders with oxygen increases the risk for an explosive atmosphere if the particle size is less than 200 microns. Once again free-clay particles would present a considerable workplace risk. Based upon these risk factors the following warning is set: It is not appropriate if powder is being used for processes from a passive operation such as weighing out small amounts for mixing of a medicine for use within the institutional setting. Accordingly the formulation of the clay delivery systems described herein would overcome these limitations of using clays in powders as have been done to date by researchers.

It is to be understood that while the invention has been described in conjunction with the detailed description thereof, the foregoing description is intended to illustrate, and not limit the scope of the invention, which is defined by the scope of the appended claims. Other embodiments, advantages, and modifications are within the scope of the following claims. In addition, the contents of all patent publications discussed supra are incorporated in their entirety by this reference.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

What is claimed is:

1. A clay composition comprising:
   a two-part active excipient clay delivery system comprising a first part and a second part; and
   optionally an additional therapeutic agent;
   wherein the first part comprises from more than 20 wt. % to 50 wt. % of sterilized clay, suspending agent(s), from more than 10 wt. % to 25 wt. % of at least two nonionic block EO-PO copolymers, and optionally a gellant; and
   wherein the second part comprises from more than 10 wt. % to 35 wt. % of at least one nonionic block EO-PO copolymer in a pH neutral water-based system, and
   wherein the ratio of the first part to the second part is from about 1:1 to about 9:1.

2. The composition of claim 1, wherein the therapeutic agent is an antimicrobial agent.

3. The composition of claim 1, wherein the therapeutic agent comprises hydroxytyrosol and/or oleuropein.

4. The composition of claim 1, wherein the composition is in the form of an ointment, cream, lotion, solution, suspension, emulsion, paste, gel or gel sheet, or syrup.

5. The composition of claim 1, wherein the composition further comprises additional additives comprising solvents, emulsifiers, viscosity adjusting agents, additional nonionic surfactants, preservatives, moisturizers, fragrances, colors, irritant-mitigating additives, pH adjusters, absorbents, anti-caking agents, anti-foaming agents, astringents, binders, buffering agents, chelating agents, or combinations thereof.

6. The composition of claim 1, wherein the therapeutic agent comprises an antibiotic, a steroid, an antifungal, an antiviral, an antihistamine, or combinations thereof.

7. The composition of claim 1, wherein the composition reduces the time required for healing of a wound.

8. The composition of claim 1, wherein the first part and the second part of different viscosities.

9. The composition of claim 8, wherein the first part has a viscosity between about 20,000 centipoise (cP) to about 50,000 cP, and the second part has a viscosity between about 5,000 cP to less than about 20,000 cP.

10. A method for delivering a clay composition for topical applications of use comprising:

combining parts of a two-part active excipient clay composition, wherein the first part comprises from more than 20 wt. % to 50 wt. % of clay, glycerin, from more than 10 wt. % to 25 wt. % of at least two nonionic block EO-PO copolymers, and optionally a gellant, and wherein the second part comprises from more than 10 wt. % to 35 wt. % of at least one nonionic block EO-PO copolymer in a pH neutral water-based system, and wherein the ratio of the first part to the second part is from about 1:1 to about 9:1;

accelerating the release of the clay into the water-based system;

activating the clay; and delivering the clay composition to a surface.

11. The method of claim 10, wherein the clay is activated upon contact of the water to the water-based system.

12. The method of claim 10, wherein the surface is a tissue or organ of the body.

13. The method of claim 10, wherein the at least one nonionic block EO-PO copolymer in the second part enhances the delivery of the clay composition to the surface.

14. The method of claim 10, wherein the nonionic block EO-PO copolymer in the first part is poloxamer 407, and the at least one nonionic block EO-PO copolymer in the second part is poloxamer 407, poloxamer 85, poloxamer 105 and/or poloxamer 188.

15. The method of claim 10, wherein the clay composition is topically applied.

16. The method of claim 10, wherein the clay composition further comprises a therapeutic agent.

* * * * *